(12) United States Patent
Taniguchi et al.

(10) Patent No.: US 8,885,037 B2
(45) Date of Patent: Nov. 11, 2014

(54) DEFECT INSPECTION METHOD AND APPARATUS THEREFOR

(75) Inventors: Atsushi Taniguchi, Fujisawa (JP);
Yukihiro Shibata, Fujisawa (JP);
Taketo Ueno, Kawasaki (JP); Toshihiko Nakata, Hiratsuka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 507 days.

(21) Appl. No.: 13/375,239

(22) PCT Filed: Jul. 1, 2010

(86) PCT No.: PCT/JP2010/004336
§ 371 (c)(1),
(2), (4) Date: Dec. 5, 2011

(87) PCT Pub. No.: WO2011/001687
PCT Pub. Date: Jan. 6, 2011

(65) Prior Publication Data
US 2012/0092484 A1    Apr. 19, 2012

(30) Foreign Application Priority Data

Jul. 1, 2009    (JP) ................. 2009-156975

(51) Int. Cl.
| | | |
|---|---|---|
| H04N 9/47 | (2006.01) |
| G01J 4/00 | (2006.01) |
| G01N 21/00 | (2006.01) |
| G06K 9/00 | (2006.01) |
| G01N 37/00 | (2006.01) |
| G01N 21/95 | (2006.01) |
| G01N 21/956 | (2006.01) |

(52) U.S. Cl.
CPC .......... G01N 21/956 (2013.01); G01N 21/9501 (2013.01)

USPC .......... 348/87; 356/364; 356/237.4; 382/149; 702/81

(58) Field of Classification Search
USPC ............................................................ 348/87
See application file for complete search history.

(56) References Cited

U.S. PATENT DOCUMENTS 5,764,363 A * 6/1998 Ooki et al. ..................... 356/364
8,274,652 B2 * 9/2012 Urano et al. ............... 356/237.4
(Continued)

FOREIGN PATENT DOCUMENTS

| JP | 5-23620 | 4/1993 |
| JP | 7-43322 | 5/1995 |

(Continued)

Primary Examiner — Hee-Yong Kim
(74) Attorney, Agent, or Firm — Antonelli, Terry, Stout & Kraus, LLP.

(57) ABSTRACT

To effectively utilize the polarization property of an inspection subject for obtaining higher inspection sensitivity, for the polarization of lighting, it is necessary to observe differences in the reflection, diffraction, and scattered light from the inspection subject because of polarization by applying light having the same elevation angle and wavelength in the same direction but different polarization. According to conventional techniques, a plurality of measurements by changing polarizations is required to cause a prolonged inspection time period that is an important specification of inspection apparatuses. In this invention, a plurality of polarization states are modulated in micro areas in the lighting beam cross section, images under a plurality of polarized lighting conditions are collectively acquired by separately and simultaneously forming the scattered light from the individual micro areas in the individual pixels of a sensor, whereby inspection sensitivity and sorting and sizing accuracy are improved without reducing throughput.

10 Claims, 19 Drawing Sheets

(56) References Cited

U.S. PATENT DOCUMENTS

2008/0015802 A1* 1/2008 Urano et al. .................. 702/81
2008/0068593 A1 3/2008 Nakano et al.
2009/0290783 A1* 11/2009 Sakai et al. .................. 382/149

FOREIGN PATENT DOCUMENTS

| JP | 8-5569 | 1/1996 |
| JP | 10-90192 | 4/1998 |
| JP | 2008-96430 | 4/2008 |

\* cited by examiner

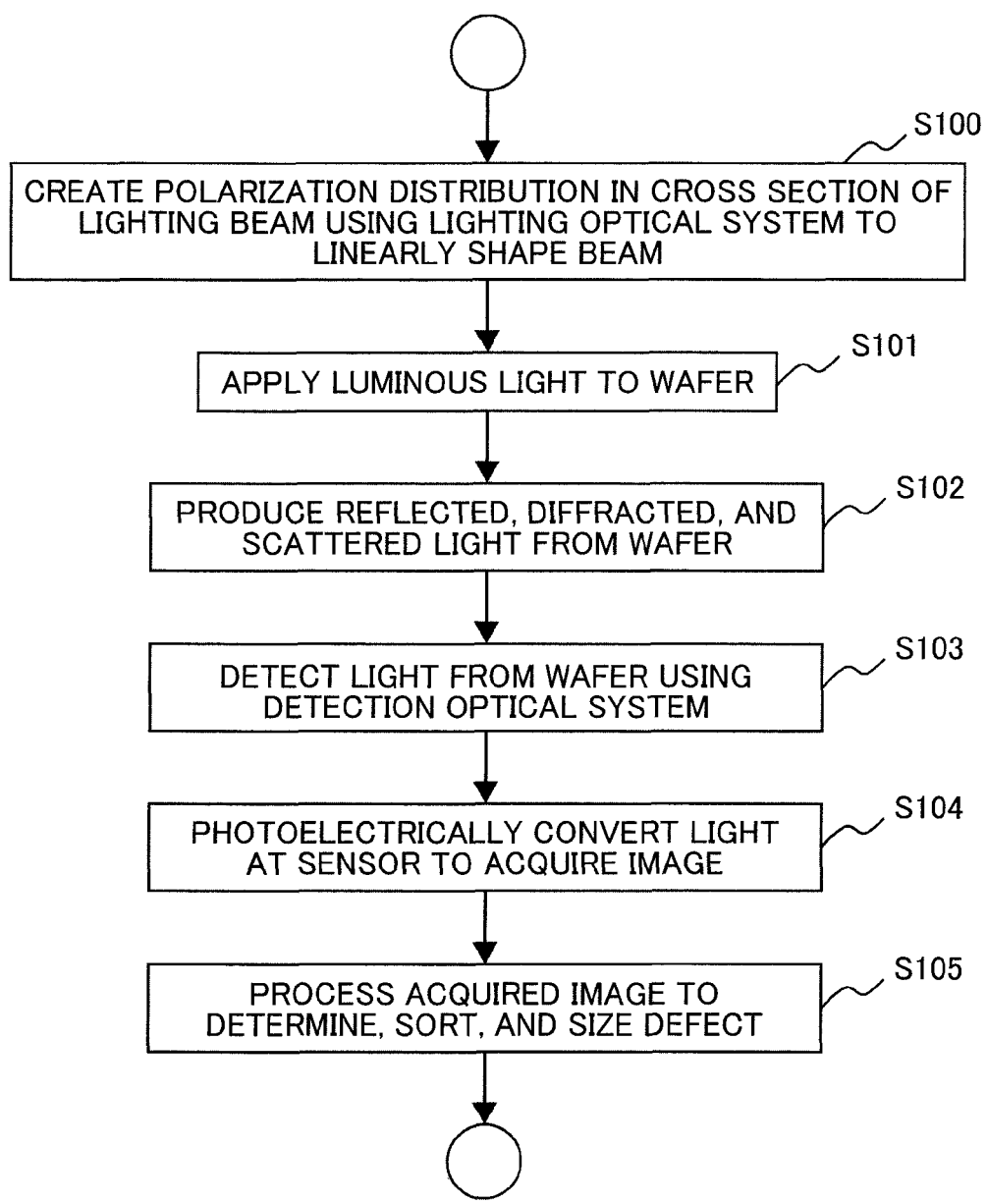

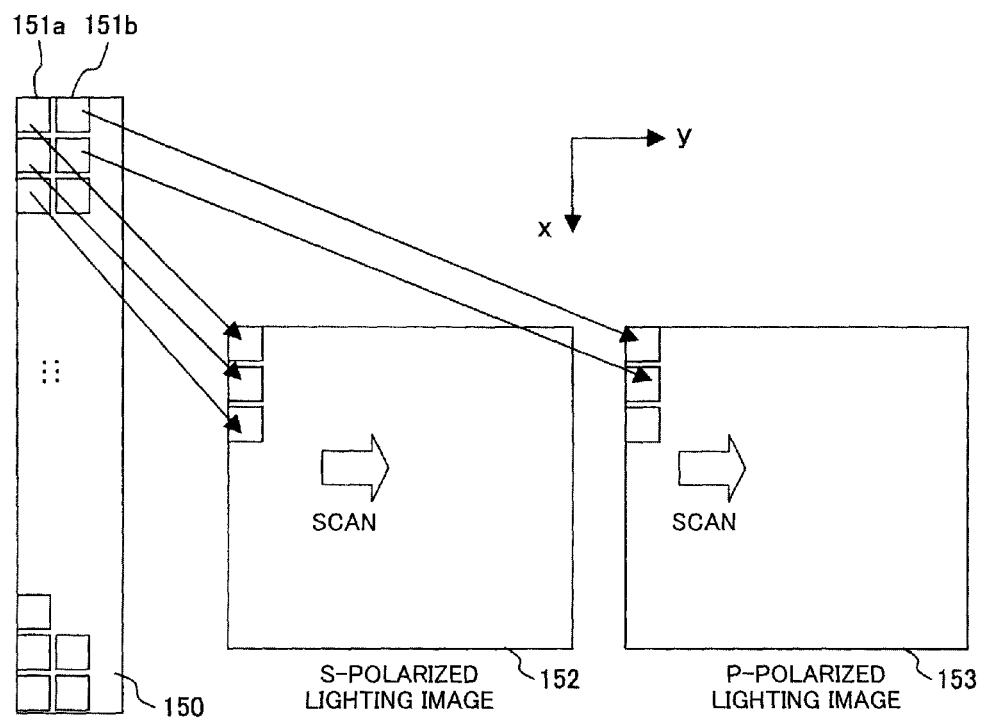

Y-AXIS DIRECTION ON WAFER

DEFECT INSPECTION METHOD AND APPARATUS THEREFOR

BACKGROUND OF THE INVENTION

The present invention relates to an inspection method for foreign substances or defects produced in fabricating an LSI and a liquid crystal substrate and an apparatus therefor.

With the downscaling of semiconductor devices, the size of defects or foreign substances on a fine pattern that is an inspection object is a few nanometers or less. Since the size of defects or foreign substances that are objects for detection becomes thus smaller, reflected, diffracted, and scattered light from these defects and foreign substances are really weak, and it is difficult to optically detect them. Thus, such a method is proposed in which plural images are acquired under pluralities of lighting conditions and detection conditions (detection orientation, detection elevation angles, and polarization detection) and these images are used to improve defect detection sensitivity, using the fact that reflected, diffracted, and scattered light from defects or foreign substances depend on the luminous light conditions (lighting orientation, lighting elevation angles, wavelengths, and polarization).

For inspection methods for defects or the like produced on a semiconductor wafer using the method above, there are methods described in Japanese Patent No. 4,001,653 and Japanese Patent Application Laid-Open Publication No. 2008-096430.

The method described in Japanese Patent No. 4,001,653 describes a defect inspection method and an apparatus therefor in which in order to find defects on inspection points on a first pattern on a sample, a reference is made to at least one known inspection response of a second pattern in the same design. Such a technique is described that in inspection, it is important to use equivalent observation points on the first and second pattern on the sample, at least one search is performed to produce at least two inspection responses, these two responses (typically, response signals from a dark field and a bright field) are separately detected by a photoelectric scheme and separately compared with each other, and differential signals are individually formed (between the first and second pattern). Namely, first and second responses on the first pattern are detected, and the results are individually compared with two responses from the same corresponding inspection points on the second pattern, and first and second differential signals between the responses are formed as the results. The differential signals individually formed are processed into data in order to determine a first pattern defect list collectively. More specifically, these first and second differential signals are collectively processed into data to determine a unified first pattern defect list. Alternatively, the first pattern defect list is subjected to data processing later. Known, harmless false defects observed on a sample surface are then extracted and removed. On the other hand, such known, harmless false defects are provided to a user for reference. A variety of inspection searches are added to increase inspection responses, and two optical responses or more are obtained for processing. Thus, inspection accuracy is further improved. In addition to this, it is described that for a transparent sample, a photoelectric detector is provided on the rear side of the sample and inspection responses of transmitted light are collected, so that the accuracy of the pattern defect list can be further improved, and defects buried in the inside of the sample can also be found. However, there is no specific description to obtain two responses.

There are problems in that the distributions of reflected, diffracted, scattered light from a defect on a semiconductor wafer are varied depending on the size and shape of the defect and on the surface topology of the wafer and the defect detection performance of a single detector depends on types of defects. The method described in Japanese Patent Application Laid-Open Publication No. 2008-096430 provides a method of addressing the problems in which light is applied to a semiconductor wafer obliquely to the normal of the wafer, reflected, diffracted, and scattered light from the wafer are detected in almost the entire hemispherical area as the target object is placed on the bottom, and the lights are used to detect and distinguish defects. The method further describes that similar polarized light or different polarized light is applied from plural directions at the same time, and plural polarization components are individually detected to reveal defects using the difference in the polarization characteristics between defects and noise.

When the size of an inspection object is a few nanometer size, the polarization characteristics of the inspection object are greatly varied depending on slight differences in the characteristics of the micro structure and medium of the inspection object. Consequently, the states of polarization of lighting and detection are appropriately selected to expect the improvement of defect detection sensitivity.

However, the optical defect inspection apparatuses according to the conventional techniques use the schemes of processing plural images obtained under pluralities of lighting conditions (lighting orientation, lighting elevation angles, wavelengths, and polarization) and detection conditions (detection orientation, detection elevation angles, and polarization detection). However, the polarization of lighting, which is one of the conditions, is not always efficiently used.

In order to efficiently use the polarization characteristics of an inspection object, it is necessary that light in the same direction and with the same angle of elevation and the same wavelength but a different polarization in polarized light be applied and differences between reflected, diffracted, and scattered light from the inspection object due to polarized light be observed. When this is performed in the conventional techniques, plural measurements, in which polarized lights are switched, are necessary to increase a detection time period that is an important specification of the inspection apparatus.

CITATION LIST

Patent Literature

Patent Literature 1: Japanese Patent No. 4,001,653
Patent Literature 2: Japanese Patent Application Laid-Open Publication No. 2008-096430

SUMMARY OF THE INVENTION

The present invention is to provide a defect inspection method and an apparatus therefor that can address the aforementioned problems of the conventional techniques, in which plural states of polarization are modulated in micro areas in the cross section of a lighting beam, and scattered lights from the micro areas are separately and simultaneously imaged on the pixels of a sensor for collectively acquiring images under plural polarization lighting conditions, whereby allowing plural types of measurements under different polarization conditions with no increase in a detection time period.

In order to address the aforementioned problems of the conventional techniques, the present invention is to provide a configuration of combining a lighting optical system capable of applying light in different states of polarization inside a illuminating region at single illumination at the same time and a detection optical system capable of detecting the different states of polarization, in a lighting optical system of an optical defect inspection apparatus.

Namely, in the present invention, an inspection apparatus includes: a lighting unit configured to illuminate a sample with light; an imager having plural detection pixels and configured to detect scattered light emanated from a portion on the sample illuminated by the lighting unit; and a signal processor configured to process a signal output from the imager by the detection of the scattered light. The lighting unit includes a polarization condition setting unit configured to illuminate plural small regions on the sample under different polarization conditions, the imager individually detects each of the small regions under the different polarization conditions at different pixels, and the signal processor processes a detected signal in each of the small regions under the different polarization conditions detected at the different pixels and detects a defect on the sample.

Moreover, in the present invention, an inspection apparatus includes: a low angle lighting unit configured to apply a first illumination of light to a sample from a first elevation angle direction; a high angle lighting unit configured to apply a second illumination of light to the sample from a second elevation angle direction; a low angle imager having plural detection pixels and configured to detect light scattered in a third elevation angle direction from a portion on the sample illuminated with the light from the low angle lighting unit or the high angle lighting unit; a high angle imager configured to detect scattered light scattered in a fourth elevation angle direction from the portion on the sample illuminated with the light from the low angle lighting unit or the high angle lighting unit; and a signal processor configured to process signals output from the low angle imager and the high angle imager by the detection of the scattered light and detect a defect on the sample. The low angle lighting unit and the high angle lighting unit include a polarization condition setting unit configured to illuminate plural small regions in a region on the sample to which the lights emitted from the low angle lighting unit and the high angle lighting unit are illuminated under different polarization conditions, the low angle imager individually detects each of the small regions under the different polarization conditions at different pixels, and the signal processor processes the detected signal in each of the small regions under the different polarization conditions detected at the different pixels of the low angle imager and signals detected using the high angle imager and detects a defect on the sample.

Furthermore, in the present invention, a method includes: illuminating a sample to be inspected with light emitted from a lighting unit; detecting light scattered from a portion illuminated by the light with an imager having plural detection pixels; and processing a signal output from the imager by the detection of the scattered light with a signal processor to detect a defect on the sample. The light illuminates plural small regions on the sample to which the light illuminates under different polarization conditions by the small regions, the imager detects light scattered from each of the small regions, which are illuminated under the different polarization conditions by the step of illuminating, with different pixels, and the signal processor processes a detected signal in each of the small regions under the different polarization conditions detected at the different pixels in the step of detecting and detects a defect on the sample.

According to an aspect of the present invention, it is possible to improve inspection sensitivity using images under plural polarization lighting conditions with no decrease in inspection throughput, and it is possible to improve defect sorting performance.

These and other objects, features and advantages of the invention will be apparent from the following more particular description of preferred embodiments of the invention, as illustrated in the accompanying drawings.

BRIEF DESCRIPTION OF THE DRAWINGS

FIG. 2 is a flowchart illustrating an inspection flow according to the first embodiment;

FIG. 3C is a diagram illustrating the relationship between polarized lighting image regions and image forming regions of the sensor according to the first embodiment;

DESCRIPTION OF THE PREFERRED EMBODIMENTS

In the following, embodiments of the present invention will be described.

First Embodiment

A first embodiment of the present invention will be described with reference to FIGS. 1 to 7. In the following, inspection performed by a dark field inspection apparatus for a semiconductor wafer will be described as an example.

Figure 1:
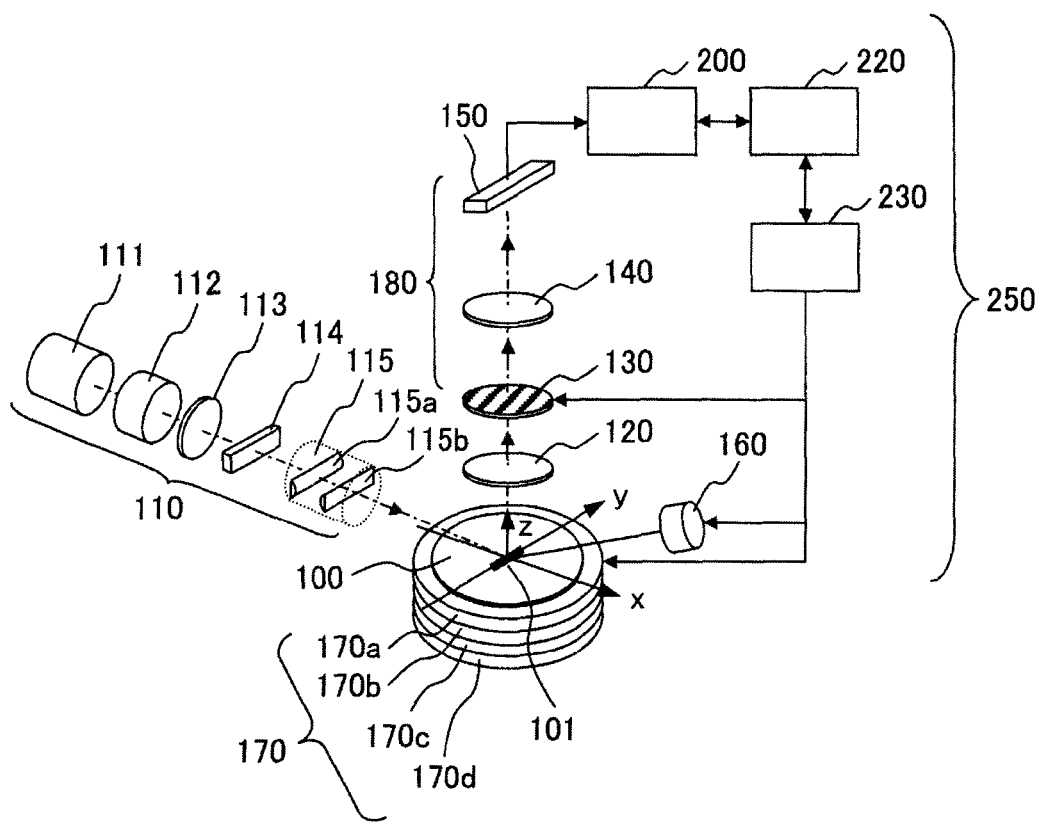
FIG. 1 is a block diagram illustrating the schematic configuration of an optical system according to a first embodiment.

FIG. 1 shows the outline of the configuration of an optical dark field inspection apparatus. The dark field inspection apparatus according to this embodiment is mainly configured of a lighting optical system 110, a stage unit 170, a detection optical system 180, and a signal processing and control system 250. The lighting optical system 110 includes a light source 111, a beam shaper 112, a polarization control device 113 formed of a polarizer or a wave plate, a polarization control device array 114 that provides a distribution of polarization of light in a cross section of a beam, and a lens 115 that images the polarization distributed light in the cross section of the beam on an inspection object (a semiconductor wafer). The stage unit 170 is configured to include an x-stage 170a, a y-stage 170b, a z-stage 170c, and a e-stage 170d that are movable. A semiconductor wafer 100 is placed on the X-stage 170a. Fine patterns are formed on the wafer 100.

The detection optical system 180 includes an objective lens 120, an image forming lens 140, a spatial filter 130 and a line sensor 150. The image forming lens 140 forms an image of light passed through the objective lens which is reflected, diffracted, and scattered from the semiconductor wafer 100 placed on the x-stage 170a and illuminated by the lighting optical system 110. The spatial filter 130 cut off a diffracted light pattern produced from repeated patterns of semiconductor patterns. The line sensor 150 detects the image of the scattered light formed by the image forming lens 140 and passed through the spatial filter 130. The signal processing and control system 250 is configured of an image processor 200 that processes an image acquired by detecting the image of light formed by the image forming lens 140 with the line sensor (TDI: Time Delay Integration image sensor), a manipulating unit 220 that manipulates the apparatus, a controller 230 that controls the individual components of the apparatus, and an auto-focusing unit 160.

FIG. 2 shows the outline of an inspection flow in which the optical dark field inspection apparatus shown in FIG. 1 is used to inspect the semiconductor wafer 100 having fine patterns thereon that is the sample of an inspection object for detecting defects on the surface. First, the lighting optical system 110 forms a distribution in polarization in the cross section of a lighting beam and linearly shapes the beam (S100). The lighting optical system 110 applies the linearly shaped lighting beam to the wafer 100 which is continuously moving in the y-direction by the y-stage 170b (S101). The linearly shaped lighting beam is applied to the wafer 100 to produce reflected, scattered, and diffracted light from the wafer 100 (S102). The reflected, scattered, and diffracted light from the wafer 100 are detected by the detection optical system 180 (S103). Images are acquired from photoelectrically converted signals output from the line sensor 150 which detects the image of light formed by the image forming lens and position information of the wafer 100 in the x-direction (S104). The acquired images are processed to detect defects (determine), classify the detected defects (sort), and size the detected defects (size), and so on (S105).

Next, the operations of the individual components will be described. First, in the process steps in which a beam emitted from the light source 111 is linearly shaped (S100) and the linearly shaped beam is applied to the wafer 100 (S101), a linearly polarized light beam emitted from the light source 111 is shaped by the beam shaper 112 which is composed from a beam expander, a cylindrical lens, or the like in such a way that the beam has an elliptic cross sectional shape in a plane vertical to the optical axis. The polarization control device 113 and the polarization control device array 114 form the shaped beam to have two kinds of different states of polarization in the minor axial direction of the ellipse (the detail will be described later). A linearly shaped beam 101 (the y-direction is the longitudinal direction) having two kinds of different states of polarization in the x-direction is applied to the wafer 100 by reduction-imaging the linearly shaped beam 101 by the lens group 115 having cylindrical lenses 115a and 115b, for example.

Subsequently, in the detection steps (S103) in which the reflected, scattered, and diffracted light produced from the wafer 100 (S102) by the irradiation of the linearly shaped beam 101, the polarization states of which is adjusted, are detected by the detection optical system 180 (S103). The reflected, scattered, and diffracted light produced from the wafer 100 are collected at the objective lens 120, and diffracted light patterns formed by scattered light from repeated patterns formed on the wafer 100 are shielded by the spatial filter 130 disposed at a pupil position on the outgoing side of the objective lens 120 or at a position equivalent to the pupil position. The scattered light not shielded by the spatial filter 130 is transmitted through the image forming lens 140, and imaged on the detection surface of the line sensor 150. The relationship between the detection surface of the line sensor 150 and a scattered light image imaged on the line sensor 150 will be described with reference to FIGS. 3A to 3C.

Figure 3A:
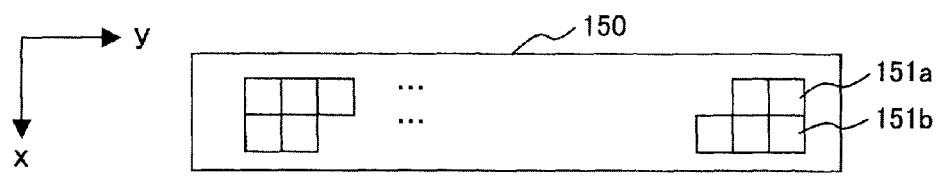
FIG. 3A is a plan view illustrating the detection surface of a line sensor, showing the state of arranging pixels on the two-line detection surface of the line sensor according to the first embodiment.
Figure 3B:
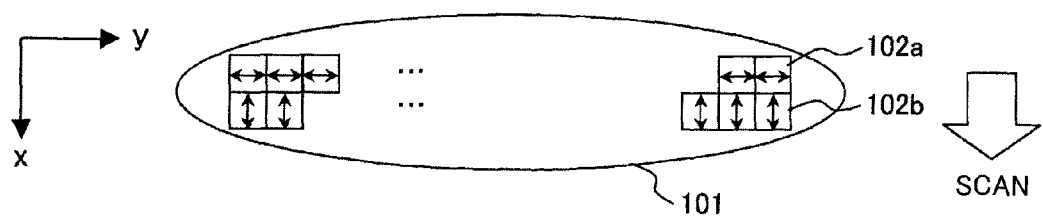
FIG. 3B is a scattered light image illustrating the distribution of states of polarization in the cross section of a scattered light beam formed on the detection surface of the line sensor according to the first embodiment.

FIG. 3A shows a state in which pixels 151a and 151b are arranged in two lines on the detection surface of the line sensor 150. On the other hand, FIG. 3B shows the distribution of states of polarization in the cross section of a scattered light beam imaged on the detection surface of the line sensor 150. The positions of the image forming lens 140 and the line sensor 150 are adjusted in such a way that the scattered light distributed as shown in FIG. 3B is laid on the detection surface of the line sensor shown in FIG. 3A. In this state, an image of the scattered light produced from the wafer is imaged on the detection surface of the line sensor 150, the pixel 151a of the line sensor 150 detects a micro area 102a of the image of the scattered light, and the pixel 151b of the line sensor 150 detects a micro area 102b of the image of the scattered light. The wafer 100 is scanned by continuously moving the wafer 100 in the y-direction at a constant speed by the stage unit 170. An image is acquired at movements at every two pixel pitches in the scanning direction, and this is repeated for the number of stages of the TDI image sensor. Signals at every two pixel pitches are added to acquire two kinds of images simultaneously which are mutually different in polarization states of the scattered light from the wafer 100 in applying two kinds of different polarized lights (S-polarized light and P-polarized light in this example) as shown in FIG. 3C. In these operations, the diffracted light from the normal patterns of the wafer are cut off by the spatial filter 130, and only signals detecting the scattered light from a defect are detected.

Subsequently, in the step of processing acquired images to detect defects (determine), classify the detected defects (sort), and size the detected defects (size) and so on (S105), in the signal processing and control system 250, two acquired images (an inspection image and an image (a reference image) acquired by imaging an adjacent pattern or an adjacent die, which is originally expected to be the same image with the inspection image) are sent to the image processor 200. These two images are compared with each other to extract defect candidates, and the extracted defect candidates are determined whether to be a defect, classifying the detected defects (sorted), and sizing the detected defects (sized). Since these two images are different only in lighting polarization conditions among large numbers of lighting conditions and detection conditions, the polarization characteristics of an inspection object are strongly reflected in these two images. Thus, these two images are used at the same time to improve defect determination performance.

Figure 4A:
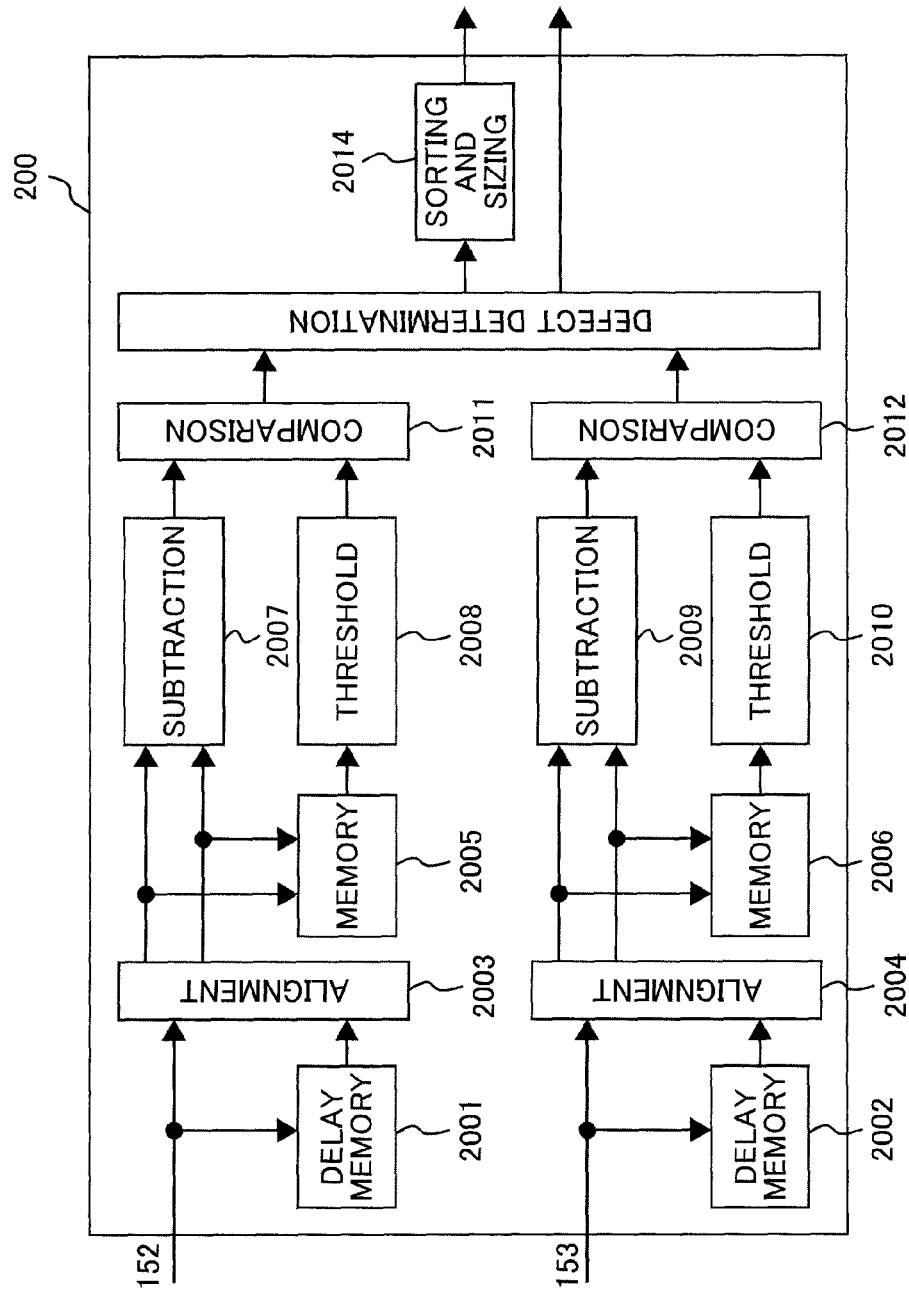
FIG. 4A is a block diagram illustrating the schematic configuration of an image processor according to the first embodiment.

The operation and effect of the present invention will be described along with the detail of the image processor 200. In the optical dark field inspection apparatus, a large number of images are acquired while scanning the wafer (while continuously moving the wafer 100, the lighting optical system 110, and the detection optical system 180 relatively in one direction). As shown in FIG. 4A, at aligning units 2003 and 2004, images 152 and 153 of a die to be inspected, which are acquired at the line sensor 150, are aligned with images of a die acquired by previously inspecting the die and recorded in delay memories 2001 and 2002 respectively, the results are temporarily stored in memories 2005 and 2006, and then differential images of these images are individually extracted (subtracted) at subtracters 2007 and 2009. In these operations, since the scattered light from a defect is different from scattered light from a normal portion, an image enhanced in the scattered light from a defect is obtained. Since such images are acquired that normal portions are dark and defect portions are bright, the found differential images are compared with threshold images stored in threshold storage units 2008 and 2010 at comparators 2011 and 2012, and the results obtained at the comparators 2011 and 2012 are integrated at a defect determining unit 2013 for determining whether to be a defect. Threshold images stored in the threshold storage units 2008 and 2010 are determined from the statistical brightness of normal portions, for example. Here, according to Japanese Patent Application Laid-Open Publication No. 2008-096430, P-polarized light and S-polarized light, which are two polarization components orthogonal to each other, have different transmittances for an optically transparent thin film on the wafer even in the case where the lighting orientation and the angle of elevation are the same. Namely, in the case where a defect exists in the upper part and inside of or under the optically transparent thin film, the scattered light intensity of S-polarized light becomes weaker in case of a defect exists in the inside of or under the transparent film than in case of a defect exists in the upper part of the transparent film.

On the other hand, in the case of P-polarized light, there are no significant differences in the scattered light intensity between the upper part (or on) and the inside of or under (below in generic) the optically transparent thin film. At this time, the defect determining unit 2013 acquires images in applying S-polarized light and P-polarized light at the same time, extracts defect candidates by the aforementioned scheme, and determines the result that merges the defect candidates of two images as a final defect. This processing is performed to more increase the acquisition rates of defects on and below the optically transparent thin film than the case of applying only one of S-polarized light and P-polarized light.

Figure 4B:
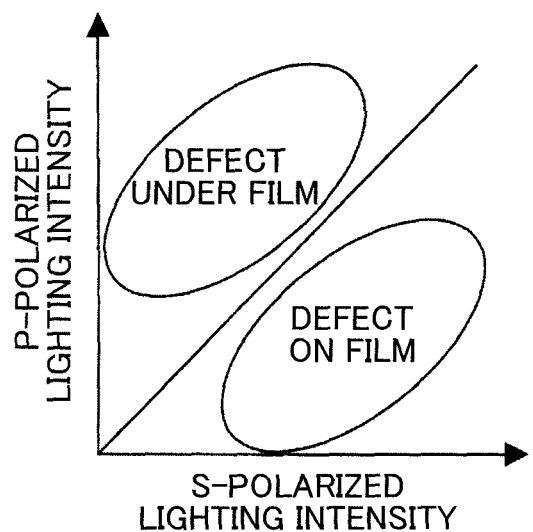
FIG. 4B a graph illustrating the scattered light intensity ratio between defects on and below a film by applying S-polarized light and P-polarized light.

The properties mentioned above are used to sort whether a defect is on the film or below the film. FIG. 4B shows the intensity ratio between applications of S-polarized light and P-polarized light. At this time, settings are made beforehand in which an intensity ratio of more than one is a defect below the film and an intensity ratio of one or less is a defect on the film, and the ratio between images acquired in applying S-polarized light and P-polarized light is taken to determine whether the intensity ratio is more than one or one or less for sorting defects. This defect sorting is performed at a sorting and sizing processing unit 2014.

Figure 4C:
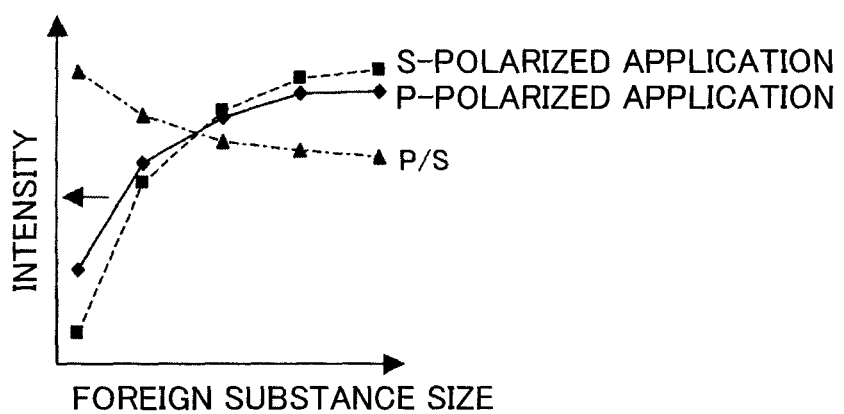
FIG. 4C is a graph illustrating the foreign substance size dependency of the scattered light intensity by applying S-polarized light and P-polarized light.

The difference between the scattered light intensities in applying S-polarized light and P-polarized light is also used for defect sizing. FIG. 4C shows a graph in which foreign substance sizes are plotted on the horizontal axis and values that the scattered light intensity is integrated in the lens aperture are plotted on the vertical axis. Since the way that the intensity changes is different in the size of foreign substances depending on application of S-polarized light and P-polarized light, the foreign substance size is determined based on the ratio between the intensities in applying S-polarized light and P-polarized light. The relationship between the foreign substance size and the scattered light intensity ratio in applying S-polarized light and P-polarized light is derived beforehand based on experiments or simulation to create a database, the ratio between images acquired in applying S-polarized light and P-polarized light is taken, and the ratio is compared with data in the database for determining the foreign substance size.

As described above, images acquired by applying S-polarized light and P-polarized light are used as they are as well as images based on the ratio between images applied with S-polarized light and P-polarized light are used, so that it is possible to effectively determine, sort, and size defects.

A gas laser, semiconductor laser, solid laser, surface emitting laser, or the like can be used for the light source 111. Infrared rays, visible rays, and ultraviolet rays can be used for wavelengths. Since optical resolutions are more improved as the wavelength becomes shortened, rays in the ultraviolet region may be used such as UV (Ultra Violet) rays, DUV (Deep Ultra Violet) rays, VUV (Vacuum Ultra Violet) rays, and EUV (Extreme Ultra Violet) rays, in observing micro defects.

Figure 5:
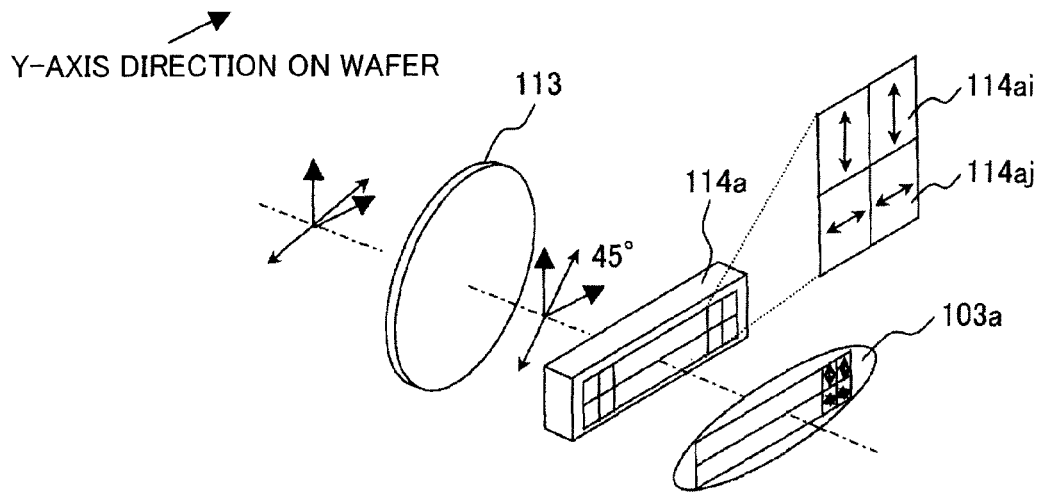
FIG. 5 is a perspective view illustrating the relationship between a polarization control device and a polarization control device array according to the first embodiment.

The detail of a method of producing a polarized distribution in the cross section of a luminous light beam will be described with reference to FIG. 5. The beam shape of a linearly polarized laser beam at a single wavelength emitted from the laser light source 111 is elliptically shaped at the beam shaper 112 by the combination of lens systems. The laser beam is transmitted through the polarization control device 113 formed of a half-wave plate (a λ/2 plate) that effectively rotates the polarization axis to produce a linearly polarized light tilted at an angle of 45 degrees from the y-axis on the wafer. The linearly polarized light enters a polarizer array 114a, which is a kind of the polarization control device array 114. The polarizer array 114a includes a polarizer 114aj that transmits components in the y-axis direction therethrough and a polarizer 114ai that transmits linearly polarized light components in the direction orthogonal to the y-axis and the optical axis (the optical axis of the lighting optical system 110) therethrough. The polarizers 114aj and 114ai are arranged in the y-axis direction, and the polarizers 114aj and 114ai are different in the direction orthogonal to the y-axis and the optical axis. The light transmitted through this polarizer array 114a has states of polarization as shown in a cross section 103a in the cross section vertical to the optical axis. The light transmitted through the wave plate array 114a is reduction-projected to the wafer by the lens 115 in such a way that the lights in the states of polarization produced by the micro wave plates are individually imaged on each one pixel of the sensor 150. Such a polarizer array 114a can be produced by arranging photonic crystals and sheet-like polarizers.

Figure 7A:
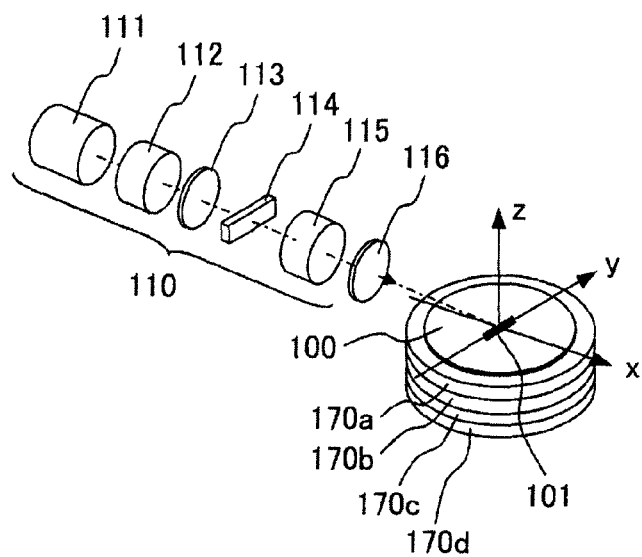
FIG. 7A is a perspective view illustrating the configuration of a lighting optical system according to the first embodiment.
Figure 7B:
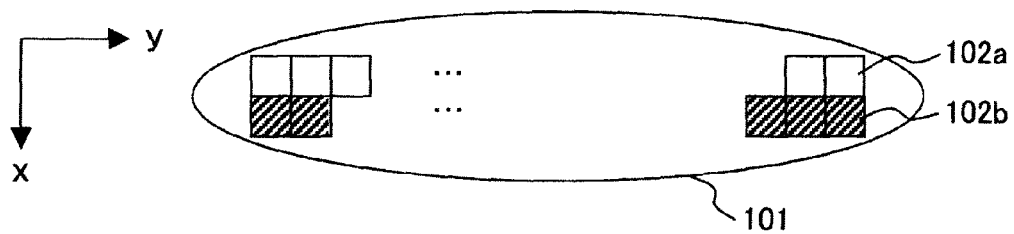
FIG. 7B is a plan view illustrating the lighting region of a wafer, showing polarization states in the lighting region on the wafer according to the first embodiment.

A method for adjusting the optical system to detect the scattered light from the wafer 100 due to luminous light having different polarization characteristics in the y-axis direction in the cross section at the pixels of the line sensor 150 will be described with reference to FIGS. 7A and 7B. First, as shown in FIG. 7A, a polarizer 116 that shields the polarization components of the light in y-axis direction among light transmitted through the polarization control device array 114 is placed on the outgoing side of the polarization control device array 114. At this time, in the application region 101 of the luminous light on the wafer 100, places applied with components polarized in the y-axis direction are dark portions 102b as shown in FIG. 7B. In detecting defects at the line sensor 150, it is sufficient to adjust the positions of the luminous light and the line sensor in such a way that the row of the pixels 151a is bright and the row of the pixels 151b is dark shown in FIG. 3A.

In this embodiment, images are taken by the line sensor (the TDI image sensor) in multi stages while continuously moving the wafer 100 in one direction. However, the timing of taking images at this time is that one image is taken at movements at every two pixels in the y-direction on the TDI image sensor. This is repeated for the number of stages of the TDI image sensor, and the result of integrating signals at every two pixel pitches is obtained as a detected signal.

In this embodiment, an example is described in which two states of polarization of light oscillating in parallel (P-polarized light) with and vertical (S-polarized light) to the y-axis on the wafer are applied at the same time. However, it is possible to similarly process images and to detect, sort, and size defects using the combination of clockwise circularly polarized light and counterclockwise circularly polarized light.

Figure 6:
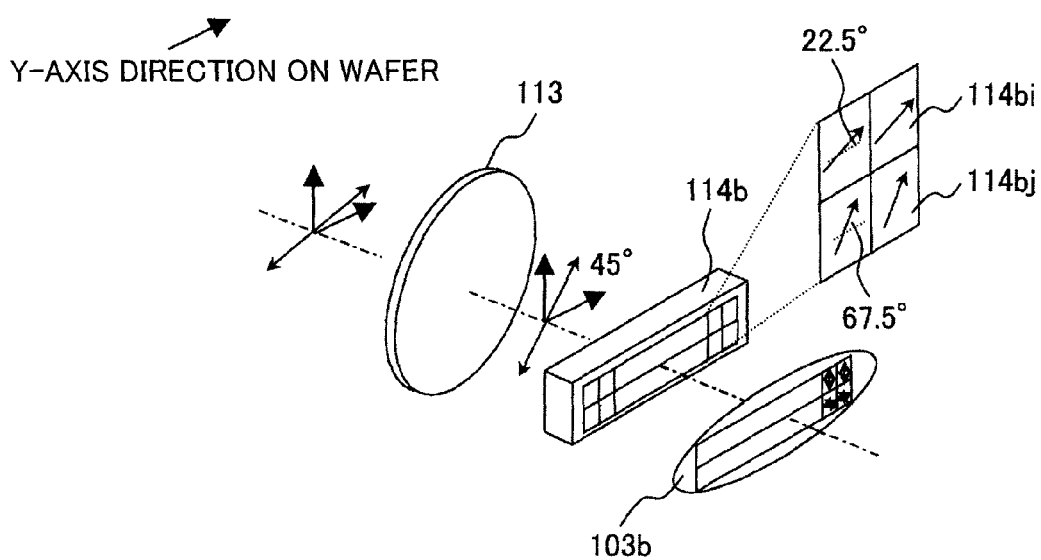
FIG. 6 is a perspective view illustrating an exemplary modification of the relationship between a polarization control device and a polarization control device array according to the first embodiment.

Subsequently, an exemplary modification of this embodiment will be described with reference to FIG. 6. This exemplary modification is different from the first embodiment in the polarization control device array 114. The detail of a method of producing a polarized distribution in the cross section of a luminous light beam will be described with reference to FIG. 6. An elliptically shaped beam at the beam shaper 112 shown in FIG. 1 is transmitted through the polarization control device 113 formed of a half-wave plate that effectively rotates the polarization axis, and a linearly polarized light tilted at an angle of 45 degrees from the y-axis on the wafer is produced. The linearly polarized light enters a wave plate array 114b, which is a kind of the polarization control device array 114. The wave plate array 114b includes a wave plate 114bi having the principal axis tilted at an angle of 22.5 degrees from the y-axis direction and a wave plate 114bj having the principal axis tilted at an angle of 67.5 degrees. The wave plates 114bj and 114bi are arranged in the y-axis direction, and the wave plates 114bj and 114bi are different in the direction orthogonal to the y-axis and the optical axis. The light transmitted through this wave plate array 114b has states of polarization as shown in a cross section vertical to an optical axis 103b. The light transmitted through the wave plate array 114b is reduction-projected to the wafer by the lens 115 in such a way that the regions polarized by the wave plates on the surface of the wafer 100, to which the light in the states of polarization produced at the micro wave plates is applied, are individually imaged on each one pixel of the sensor. This wave plate array 114b is fabricated using an electro-optic element or a magneto-optic element such as photonic crystals and liquid crystals.

In the case of using an electro-optic element or a magneto-optic element for the wave plate array 114b, it is possible to produce a given polarized distribution in the cross section of the lighting beam 103b by combining the wave plate array 114b with the orientation of the wave plate 113.

In this embodiment, the states of polarization are varied only in the scanning direction of the wafer 100. However, of course, it is also possible to vary the states of polarization in the direction in parallel with the scanning direction of the wafer. In the case where the polarized lighting conditions with high detection sensitivity are different depending on places on a detection target, it is also possible to switch polarized lights under inspection or at every inspection.

Second Embodiment

A second embodiment of the present invention will be described with reference to FIGS. 8A and 8B and FIG. 9. An optical system according to the second embodiment of the present invention is different from the optical system according to the first embodiment shown in FIG. 1 in the polarization control device array 114, the sensor array 150, and the image processor 200. In the following, differences from the first embodiment will be described.

In this embodiment, a polarization control device array 114c produces four kinds of states of polarization in a luminous light beam, and a sensor array 150 individually detects four kinds of polarization components of scattered light from polarized lights for each of four kinds of states of polarization, 16 kinds of images in total. The states of polarization can be expressed by three parameters in total, two linearly polarized light components having orientations orthogonal to each other and different at an angle of 45 degrees and a circularly polarized light component. Including the above three parameters, the states of polarization of light can be fully expressed by four kinds of parameters added with intensity in total. Consequently, 16 images, from which there can be chosen four kinds of states of polarization in the cross section of the lighting beam and four kinds of polarized light components including linearly polarized light components in orientations orthogonal to each other and different at an angle of 45 degrees and a circularly polarized light component as polarized light components to be detected, fully include information about the polarization characteristics of a wafer 100, so that it is possible to optimize defect detection sensitivity using polarized lights.

Figure 8A:
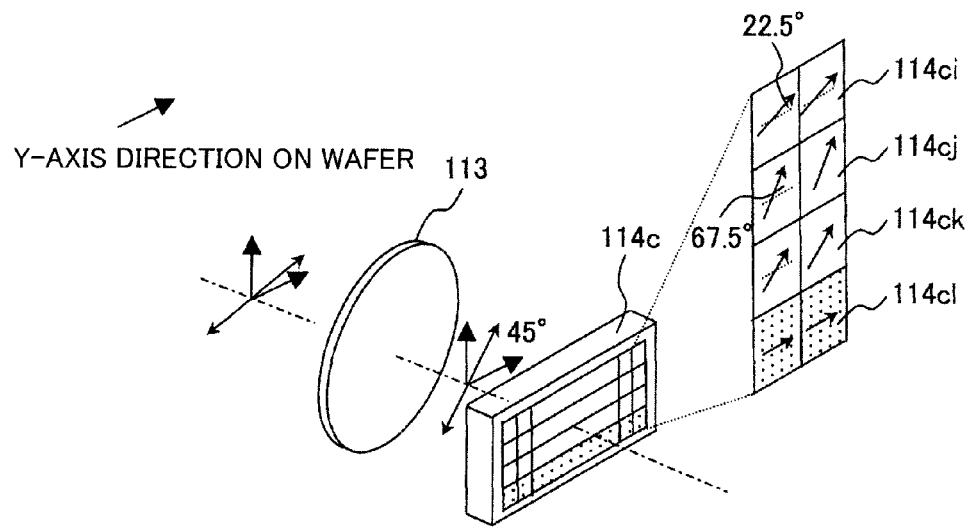
FIG. 8A is a perspective view illustrating the relationship between a polarization control device and a polarization control device array by a method according to a second embodiment.

FIG. 8A shows the polarization control device array 114c. The polarization control device array 114c includes half-wave plates 114ci, 114cj, and 114ck having the principal axis in different orientations and a quarter-wave plate 114cl, in which a linearly polarized light in the direction at an angle of 45 degrees after transmitted through a half-wave plate 113 is converted into light in four kinds of states of polarization in the direction orthogonal to the y-axis in the plane orthogonal to the optical axis of a lighting optical system 110. The polarization control device array 114c can be fabricated using an electro-optic element or a magneto-optic element such as photonic crystals and liquid crystals. The principal axis orientations of the half-wave plates 114ci, 114cj, and 114ck are at an angle of 22.5 degrees, an angle of 67.5 degrees, and an angle of 45 degrees, respectively, and the states of polarization of the transmitted light are linearly polarized lights in the y-direction, in the direction orthogonal to the y-axis, and in the direction at an angle of 45 degrees from the y-axis, respectively. Here, although the state of polarization is not changed even though the light is transmitted through the half-wave plate 114ck, the half-wave plate 114ck is provided in order to match the intensity with that of the lights after transmitted through the half-wave plates 114ci and 114cj. The half-wave plate 114cl is a quarter-wave plate having the principal axis in the y-axis direction, and the light transmitted therethrough becomes circularly polarized light.

Figure 8B:
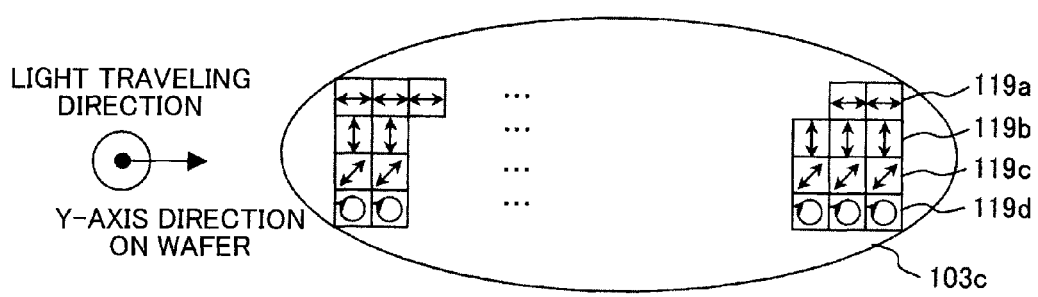
FIG. 8B is a plan view illustrating the lighting region of a wafer, showing polarization states in the lighting region on the wafer according to the second embodiment.

FIG. 8B shows the cross section of a beam transmitted through the polarization control device 114c. The state of polarization of the beam is modulated into lights 119a to 119d as the result that an elliptic beam cross section 103c is partially controlled by the half-wave plates 114ci, 114cj, and 114ck in the minor axial direction. This beam is imaged on the wafer 100 using a lens 115 (see FIG. 1), and reflected, diffracted, and scattered light from the wafer 100, to which the polarized lights 119a to 119d are applied, are individually detected by the line sensor 150.

Figure 9:
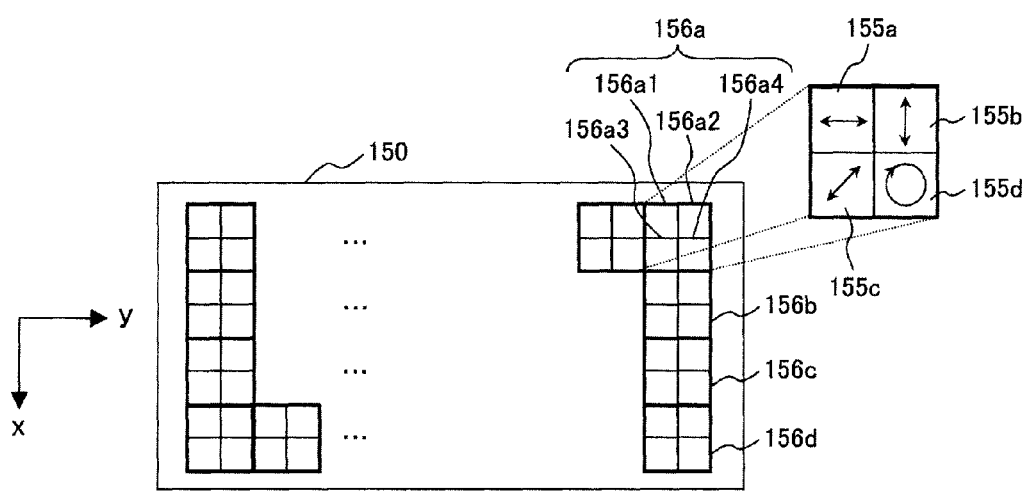
FIG. 9 is a plan view illustrating the detection surface of a line sensor, showing the state of arranging pixels of the line sensor that simultaneously and independently detects 16 inspection images according to the second embodiment.

FIG. 9 shows a sensor unit of the line sensor (the TDI image sensor) 150 for use in the second embodiment. Reflected, diffracted, and scattered light from a single polarized light 119a in the lighting beam are detected at four pixels 156a1 to 156a4 of a pixel group 156a. Four pixels 156a1 to 156a4 are attached with linear polarizers 155a to 155c having different orientations and a circular polarizer 155d for detecting polarization components. Reflected, diffracted, and scattered light from the polarized lights 119b to 119d are similarly detected at pixel groups 156b to 156d formed of four pixels. Thus, a single scan of the wafer allows simultaneous, independent acquisition of 16 inspection images in total under four kinds of polarization conditions for luminous light and four kinds of polarization conditions for detection for each of four kinds of the polarization conditions for luminous light. In this embodiment, images are taken by the line sensor (the TDI image sensor) while continuously moving the wafer 100 in one direction. However, timing of taking images at this time is that one image is taken at movements at every eight pixels on the TDI image sensor. This is repeated for the number of stages of the TDI image sensor, and the result of integrating signals at every eight pixel pitch is obtained as a detected signal.

Figure 10:
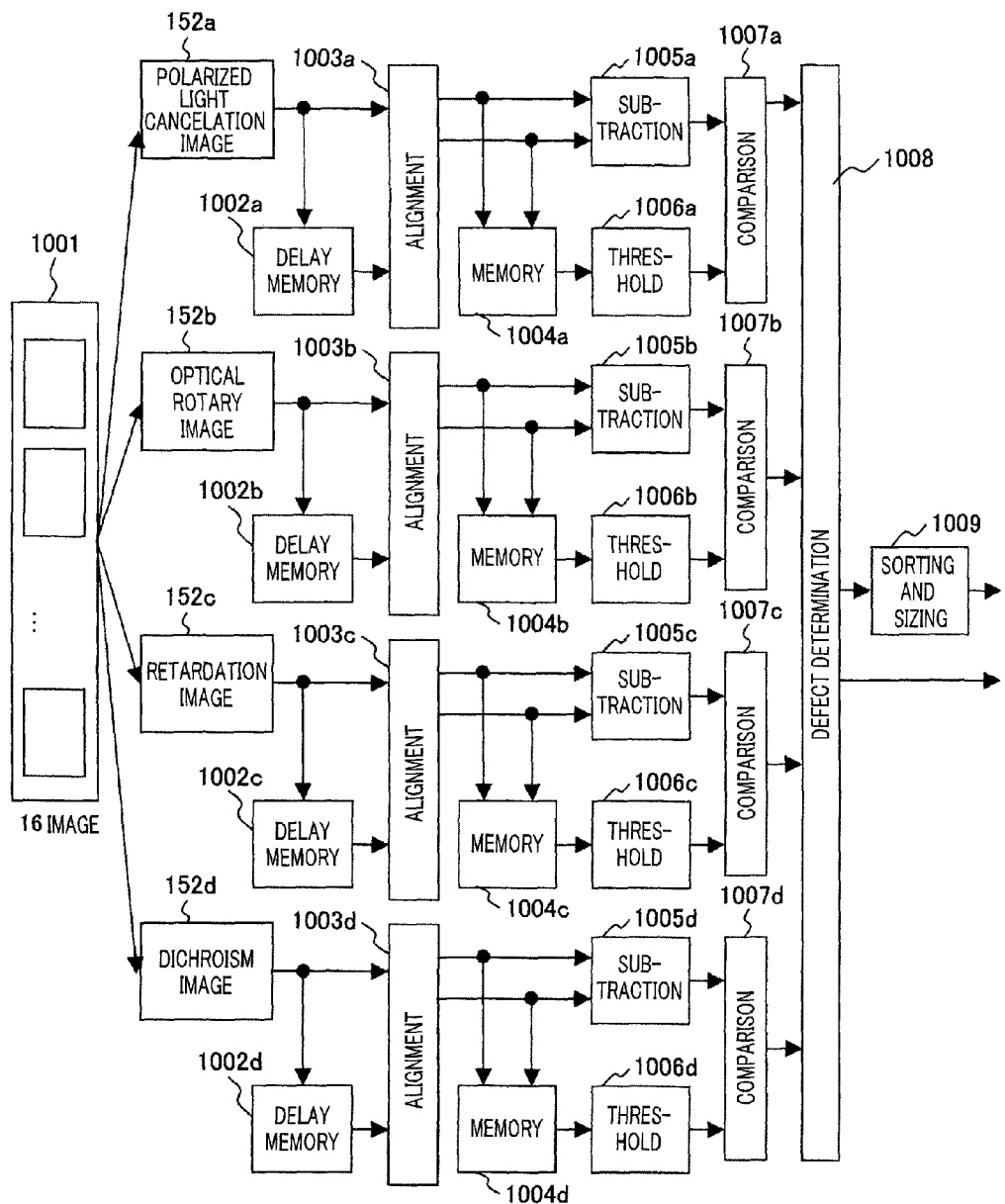
FIG. 10 is a block diagram illustrating the schematic configuration of an image processor according to the second embodiment.

A method of detecting, sorting, and sizing defects from these 16 images will be described with reference to FIG. 10. Since 16 images 1001 include information about all the polarization characteristics (all 16 terms of a Mueller Matrix) of an inspection object, it is possible to derive, from these images, images with parameters expressing polarization characteristics represented by polarization cancellation images at a polarization cancellation image calculating unit 152a, optical activity images at an optical activity image calculating unit 152b, retardation images at a retardation image calculating unit 152c, and dichroic images at a dichroic image calculating unit 152d, based on the four fundamental operations of arithmetic. The derived polarization parameter images are aligned with die parameter images previously inspected and recorded in delay memories 1002a to 1002d at aligning units 1003a to 1003d, the polarization parameter images and the die parameter images aligned with each other are stored in memory units 1004a to 1004d, and the aligned images are subtracted from each other at subtracters 1005a to 1005d to find differential images. In these operations, since scattered light from a defect has polarization characteristics different from the polarization characteristics of scattered light from a normal portion, an image enhanced in defect information is obtained.

The polarization parameter images and the die parameter images stored in the memory units 1004a to 1004d are used to find threshold images of differential images corresponding to polarization parameter images at threshold operating units 1006a to 1006d. The threshold images are compared with the differential images of the polarization parameter images calculated at the subtracters 1005a to 1005d using the comparators 1007a to 1007d, and the results compared at the comparators 1007a to 1007d are integrated at a defect determining unit 1008 for determining defects.

In this determination, defect candidates extracted from the images are merged and considered to be defects on the wafer as similar to the first embodiment. The threshold images are determined according to statistical processing using plural parameter images of normal portions. In this determination, in the case where the size of a defect is as small as a few to a few hundreds nanometers, the defect has strong polarization characteristics, and the polarization characteristics are greatly different depending on the shape and size of the defect, so that plural polarization parameters are used at the same time to improve the acquisition rate of defects.

The differences between the polarization characteristics are detected using plural polarization parameters, so that it is possible to sort and size defects at a sorting and sizing unit 1009. For example, in the case of the optical activity expressing the rotation of the polarization axis, the amount of rotation of the polarization axis is different between the normal portion and the defect portion. Thus, a threshold is set to the amount of rotation, defects with the amount of rotation at the threshold or more are considered to be defect candidates, and defects are sorted and sized according to the amount of rotation. Therefore, it is possible to detect a defect that cannot be found only by comparison of intensity.

Third Embodiment

A third embodiment of the present invention will be described with reference to FIG. 11.

Figure 11:
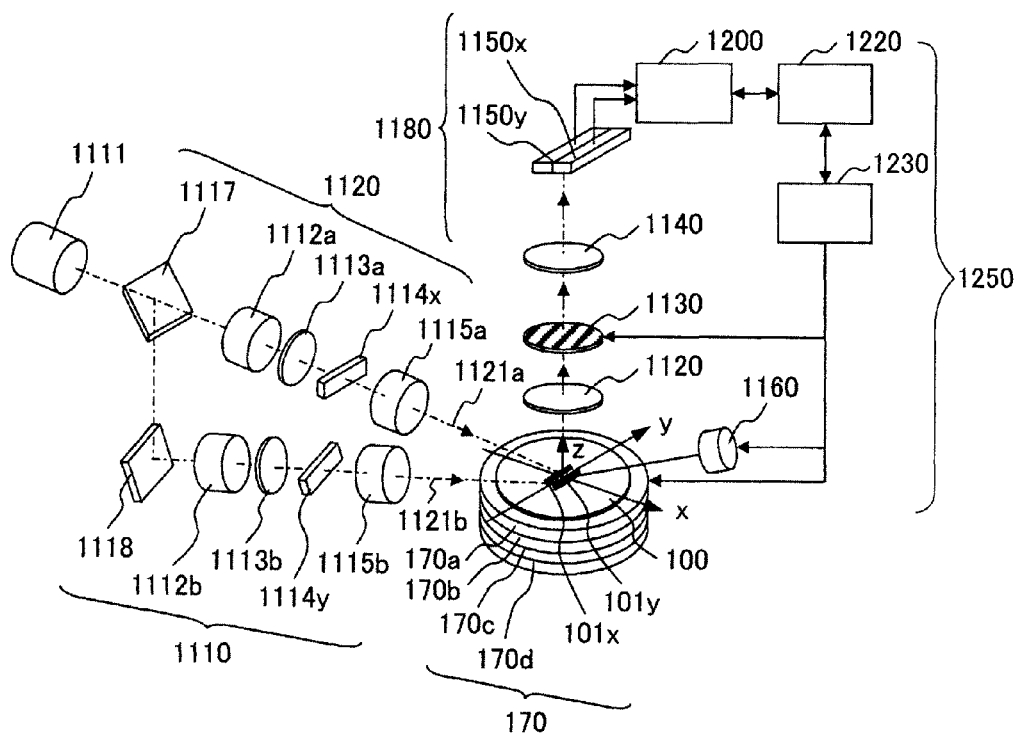
FIG. 11 is a block diagram illustrating the schematic configuration of an inspection apparatus according to a third embodiment.

FIG. 11 shows an optical system according to the third embodiment of the present invention. The third embodiment is different from the first embodiment in that there are two beams of luminous light. The system includes a light source 1111, a mirror 1117 that diverges the optical path of a laser beam emitted from the light source 1111 to two lighting optical systems 1110 and 1120, in which a semiconductor wafer 100 is obliquely illuminated by using two luminous light beams 1121a and 1121b, and a detection optical system 1180 having an objective lens 1120 and an image forming lens 1140 to image reflected, diffracted, and scattered light of the luminous light beam 1121a from the illuminated semiconductor wafer 100 on the detection surface of a line sensor 1150x and to image reflected, diffracted, and scattered light of the luminous light beam 1121b on the detection surface of a line sensor 1150y.

The detected signals are processed at a signal processing and control system 1250 including an image processor 1200, a manipulating unit 1220 that manipulates the system, a controller 1230 that controls the components of the system, and an autofocus detection system 1160. The sample 100 is placed on a stage unit 170 including an x-stage 170a, a y-stage 170b, a z-stage 170c, and a θ-stage 170d to control the position of the sample 100. The lighting optical system 1120 includes a beam shaper 1112a, a polarization control device 1113a formed of a polarizer or a wave plate, a polarization control device array 1114x that provides a light the polarization of which is distributed in the cross section of a beam, and a lens 1115a that images the light the polarization of which is distributed in the cross section of a beam on an inspection object (a semiconductor wafer). The lighting optical system 1110 similarly includes a beam shaper 1112b, a polarization control device 1113b formed of a polarizer or a wave plate, a polarization control device array 1114y that provides a light the polarization of which is distributed in the cross section of a beam, and a lens 1115b that images the polarized distribution in the cross section of a beam on an inspection object (a semiconductor wafer). The lighting optical system is formed of two systems 1110 and 1120, and the description of the operations of the components is omitted because the operations are the same as those in the first embodiment.

The number of detected images at the portions to be inspected on the wafer 100 is two times the number of detected images in the case of a single luminous light beam, and the same light application as explained in the first embodiment or the second embodiment is conducted in each of the lighting optical systems to detect and process images. Thus, it is expected to further improve the sensitivity and improve the accuracy of sorting and sizing defects. It is also possible to use three luminous light beams or more to acquire much more information. The number of states of polarization modulated in the cross section of each luminous light beam may be two kinds as in the first embodiment or four kinds as in the second embodiment, or other than these. The number can be changed depending on luminous light beams.

Fourth Embodiment

Figure 12:
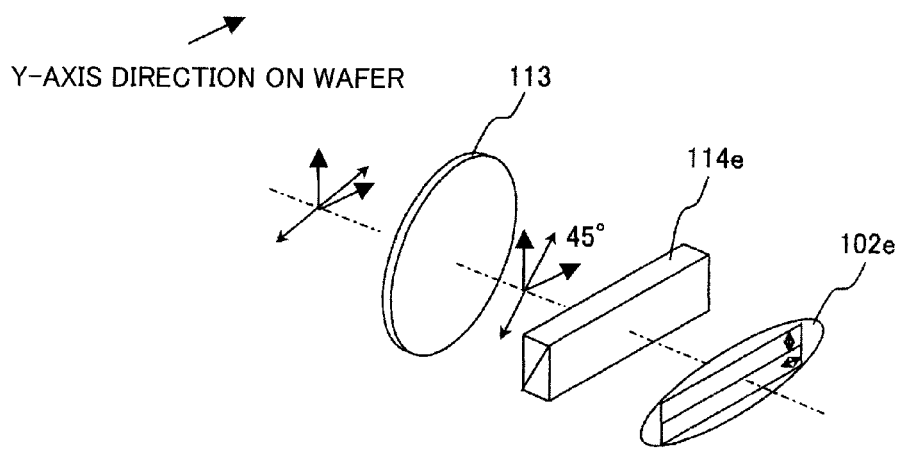
FIG. 12 is a perspective view illustrating the configuration of a lighting optical system according to a fourth embodiment.

A fourth embodiment of the present invention will be described with reference to FIG. 12. An optical system according to the fourth embodiment of the present invention is different from the optical system according to the first embodiment shown in FIG. 1 in the polarization control device array 114, the sensor array 150, and the image processor 200. In the first embodiment, the polarization control device array 114 is used to modulate the state of polarization of the luminous light in both of the x-axis and the y-axis of the wafer 100. The fourth embodiment is the case where the state of polarization of luminous light is different only in the y-axis direction on the wafer 100 shown in FIG. 1. An optical system is almost the same as the optical system shown in FIG. 1, and it is sufficient that the polarization control device array 114 is replaced by a simple polarization element. A Wollaston polarizing prism 114e is used to implement this polarization element, as shown in FIG. 12. Light from a light source is formed in a linearly polarized light tilted at an angle of 45 degrees in the orientation from the axis on the wafer by a polarization control device 113, and the light is caused to enter the Wollaston polarizing prism 114e. The Wollaston polarizing prism 114e can split the incident polarized light into two linearly polarized lights orthogonal to each other. However, since the two split lights are not in parallel with the optical axis, the lights are imaged in consideration of the tilted amount of the light beams in imaging the beams on the wafer.

Fifth Embodiment

A fifth embodiment of the present invention will be described with reference to FIG. 13.

Figure 13:
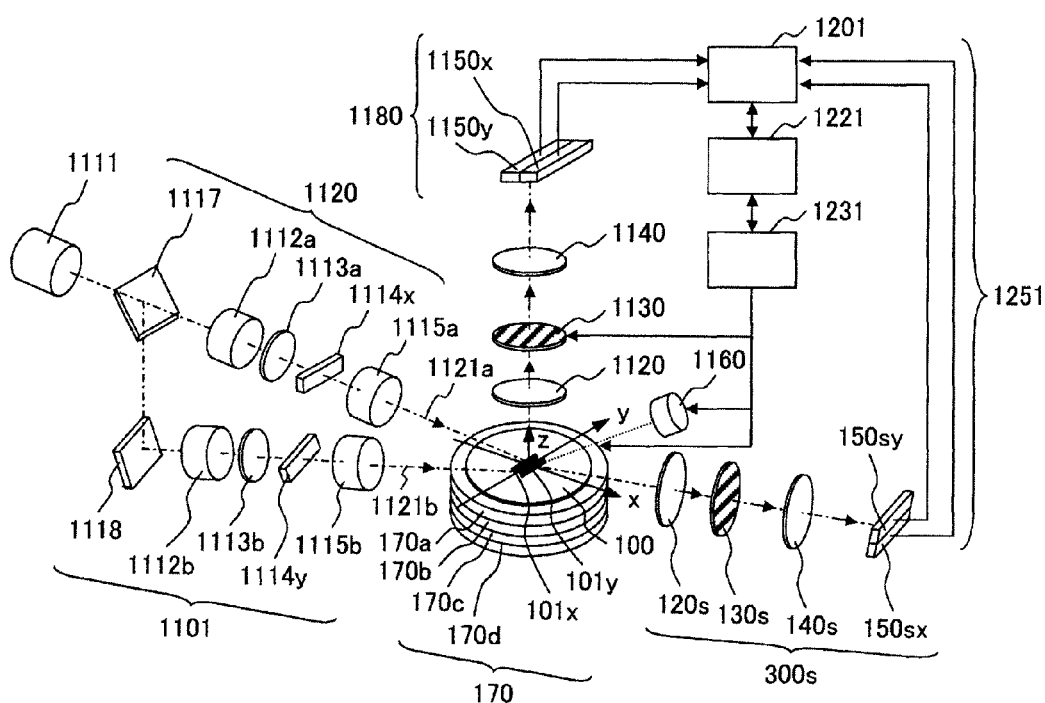
FIG. 13 is a block diagram illustrating the schematic configuration of an inspection apparatus according to a fifth embodiment.

FIG. 13 shows an optical system according to the fifth embodiment. In the fifth embodiment, an oblique detection system 300s is additionally provided in the optical system according to the third embodiment shown in FIG. 11 to obliquely detect scattered light from a wafer 100 with respect to the z-axis. The oblique detection system 300s includes an objective lens 120s and an image forming lens 140s that image reflected, diffracted, and scattered light from the wafer 100, line sensors 150sx and 150sy that respectively detect reflected, diffracted, and scattered light from two luminous light beams 101x and 101y from the wafer imaged at the objective lens 120s and the image forming lens 140, and a spatial filter 130s that removes diffracted light from semiconductor patterns. Images obtained at the line sensors 150sx and 150sy are similarly processed as images obtained at the line sensors 150x and 150y.

Here, the lights reflected, diffracted, and scattered from the wafer 100 are different in the intensity and the state of polarization depending on directions. Spherical foreign substances tend to be detected using images obtained at the line sensors 150x and 150y because the light from spherical foreign substances is strongly scattered upward, whereas concave defects tend to be detected from images obtained at the line sensors 150sx and 150sy because the light from concave defects is strongly scattered to a direction in low elevation angle. As described above, the oblique detection system 300s is additionally provided in addition to the upward detection system, so that it is possible to detect various kinds of defects. Images obtained at the upward and oblique detection system are compared with each other, so that it is also possible to sort defects in such a way that defects are foreign substances if oblique intensity is stronger than upward intensity, whereas defects are concave defects if vice versa, for example.

Sixth Embodiment

In the first to fifth embodiment described above, an inspection object is the wafer 100 having circuit patterns formed on the surface. In this embodiment, an embodiment will be described with reference to FIGS. 14A and 14B to 18, in which the present invention is applied to an optical dark field inspection apparatus whose inspection object is a flat semiconductor wafer with no patterns on the surface.

Figure 14A:
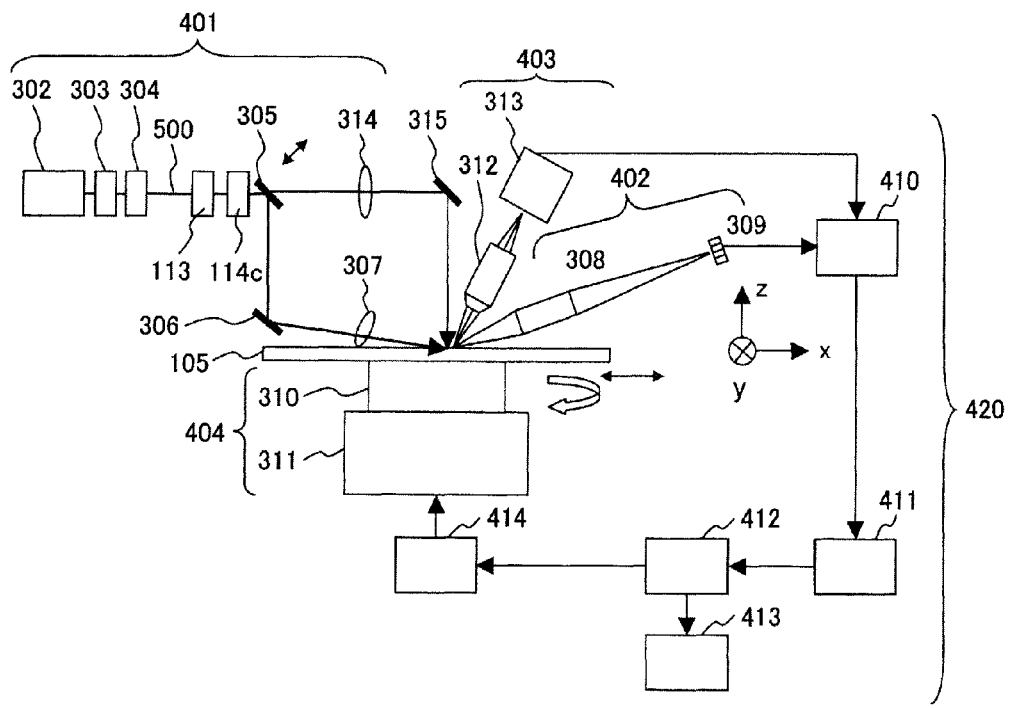
FIG. 14A is a block diagram illustrating the schematic configuration of an inspection apparatus according to a sixth embodiment.

FIG. 14A shows the schematic configuration of an optical dark field defect inspection apparatus according to a sixth embodiment of the present invention that inspects a semiconductor wafer 105 with no patterns formed on the surface. The defect inspection apparatus is configured to include a lighting optical system 401, a low angle detection optical system 402, a high angle detection optical system 403, a wafer stage 404, and a signal processing and control system 420.

Figure 14B:
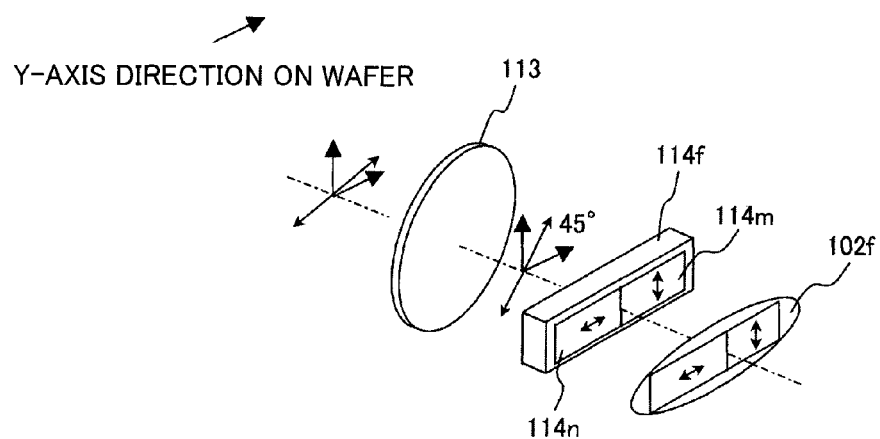
FIG. 14B is a perspective view illustrating the configuration of a lighting optical system according to the sixth embodiment.

The lighting optical system 401 includes a laser light source 302, a beam expander 303, a homogenizer 304, a wave plate 113, a polarization control device array 114, an optical path switching mirror 305, a low angle lighting mirror 306, a low angle lighting condenser lens 307, a high angle lighting condenser lens 314, and a high angle lighting mirror 315. The beam diameter of a laser beam 500 emitted from the laser light source 302 is increased at the beam expander 303, the cross sectional topology of the laser beam 500 on the surface at a right angle to the optical axis is shaped in a long, elliptical shape (in a line shape), and the laser beam 500 is converted to have a uniform illumination distribution at the homogenizer 304. As shown in FIG. 14B, the elliptically shaped beam is transmitted through the polarization control device 113 formed of a half-wave plate (a λ/2 plate) that effectively rotates the polarization axis, and a linearly polarized light is produced as tilted at an angle of 45 degrees from the y-axis on the surface of the wafer placed on the wafer stage 404. The linearly polarized light enters a polarizer array 114f, which is a kind of the polarization control device array 114. The polarizer array 114f includes a polarizer 114m that transmits components in the y-axis direction therethrough, and a polarizer 114n that transmits linearly polarized light components in the direction orthogonal to the y-axis and the optical axis of the laser beam 500. Such a polarizer array can be fabricated by arranging photonic crystals or sheet-like polarizers.

Now referring to FIG. 14A, first, the case will be described where the wafer 105 is illuminated with the linearly polarized light from a low angle. The optical path of the laser beam 500, which is transmitted through the polarizer array 114f and provided with predetermined polarization characteristics as shown in a cross section 102f, is switched downward at the optical path switching mirror 305, and the optical path is again switched at the low angle lighting mirror 306. The laser beam 500 is transmuted through the low angle illumination condenser lens 307, the cross section of the laser beam 500 is shaped in a long, elliptical shape (in a line shape), and the shaped laser beam linearly illuminates a region to be inspected on the wafer 105. Here, for the laser light source 302, it is sufficient to use a laser light source that emits a laser beam of ultraviolet (UV, DU V, VUV, EUV) rays having a wavelength of 400 nm. The beam expander 303 is an anamorphic optical system, which is configured using plural prisms. The beam diameter is changed only in one direction in each plane vertical to the optical axis, and the condenser lens is used to linearly illuminate the sample. Instead of the combination of the condenser lens 307 and the beam expander 303, such a configuration is also possible in which a beam is linearly shaped for application using a magnifier lens that magnifies the beam diameter and a cylindrical lens that reduces the diameter in one direction of the magnified beam and almost linearly shapes the cross sectional topology of the beam. The case of using the cylindrical lens is effective in that the length of the optical system can be reduced by the simple structure. The homogenizer 304 is used for providing uniform lighting intensity. However, the homogenizer 304 may be replaced by a diffracted optical element or a fly-eye lens, for example. Light may be applied with no use of the homogenizer 304. In case of the homogenizer is omitted, the attenuation of laser beam intensity will be suppressed and a strong illumination will be applied to the wafer.

Next, the case will be described where the wafer 105 is illuminated from a high angle. When a drive unit, not shown, is used to retract the optical path switching mirror 305 from the optical path of the laser beam 500, the laser beam 500, which is transmitted through the polarization control device 113 and the polarization control device array 114f and provided with the polarization characteristics, travels forward, passes through the high angle lighting condenser lens 314, and enters the high angle lighting mirror 315. The optical path of the laser beam 500 is deflected at a right angle, and the laser beam 500 linearly and vertically illuminates a region to be inspected on the wafer 105. A method of forming linear luminous light is the same as the case of applying light at a low angle as explained above.

The low angle detection optical system 402 is configured to include an image forming system 308 and a photodiode allay 309. The low angle detection optical system 402 will be described in detail with reference to FIG. 15A. The low angle detection optical system 402 is configured to include a condenser lens 321, an image intensifier 322, an image forming lens 323, and the photodiode allay 309. Light scattered from a light field 320 on the wafer 105, to which light is applied at a low angle or light is applied at a high angle from the lighting optical system 401, is collected at the condenser lens 321, and the scattered light is amplified at the image intensifier 322, and imaged on the detection surface of the photodiode allay 309 through the image forming lens 323. In these operations, since the laser beam 500 applied to the wafer 105 is shaped in such a way that the laser beam 500 has different states of polarization depending on the positions in the beam by the lighting optical system 401, the low angle detection optical system is configured to individually detect the scattered light when applied in the states of polarization using the diodes of the photodiode allay 309. Thus, it is possible to simultaneously and individually detect the scattered light when applied in the different states of polarization. Here, the image intensifier 322 is used in order to amplify a weakly scattered light from a micro defect on the wafer 105 for allowing the weakly scattered light to be detected. The photodiode allay 309 produces electric signals according to the received light quantity. The electric signals produced from the photodiode allay 309 are subjected to amplification, noise processing, and analog-to-digital conversion at an analog circuit 410 as necessary.

Figure 15A:
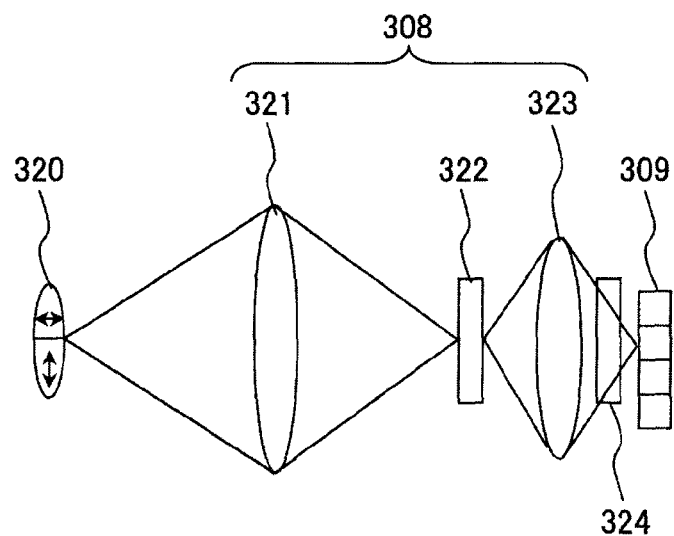
FIG. 15A is a plan view illustrating the schematic configuration of one line of a low angle detection optical system of an image forming optical system according to the sixth embodiment.
Figure 15B:
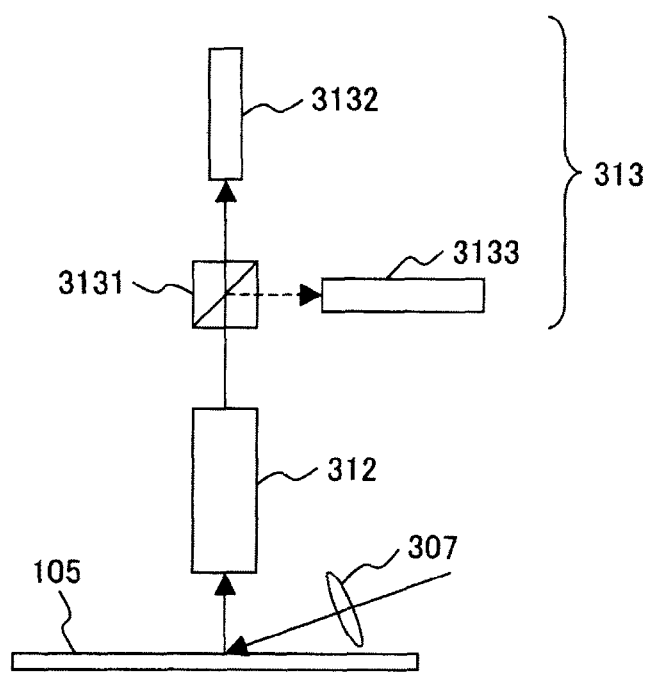
FIG. 15B is a front view illustrating the schematic configuration of one line of a high angle detection optical system of the image forming optical system according to the sixth embodiment.

The high angle detection optical system 403 is configured to combine a condensing optical system 312 with a sensor unit 313. As shown in FIG. 15B, the sensor unit 313 is configured to include a polarizing beam splitter 3131, a P-polarized light detecting photomultiplier tube 3132, and an S-polarized light detecting photomultiplier tube 3133, in which the scattered light from the wafer 105 collected at the condensing optical system 312 is split into P-polarized light components and S-polarized light components at the polarizing beam splitter 3131 for detection. In such a configuration, the laser beam 500 is shaped at the lighting optical system 401 in such a way that states of polarization are varied depending on positions in the beam, the laser beam 500 is applied to the wafer 105, and light is scattered from the wafer 105 and collected at the condensing optical system 312. The scattered light is split into P-polarized light components and S-polarized light components at the polarizing beam splitter 313, the P-polarized light components and the S-polarized light components are detected at the P-polarized light detecting photomultiplier tube 3132 and the S-polarized light detecting photomultiplier tube 3133, respectively, and the components are sent to the analog-to-digital converting unit 410 for analog-to-digital conversion. The analog-to-digital converted signals are processed at the signal processing unit 411 together with the signals detected at the low angle detection optical system

402. Plural optical signals scattered from almost the same region are added and subjected to defect determination, and a defect map is displayed at a map output unit 413 through a CPU 412.

The wafer stage 404 is configured to include a chuck (not shown) that holds the wafer 105, a rotary stage 310 that rotates the wafer 100, and a translation stage 311 that moves the wafer 100 in the radial direction (the axial direction). The wafer stage 403 spirally lights the entire surface of the sample by rotating scan and translation scan. A stage controller 414 controls rotation speed and translation speed so as to light desired regions.

It is also possible in this configuration that an analyzer 324 is provided in front of the photodiode allay 309 to extract and detect only specific polarization components. The polarization characteristics of scattered light are different between defects and wafer roughness, which is micro irregularities on the surface of the wafer 105, and the polarization characteristics greatly depend on the orientation and the angle of elevation. Thus, specific polarization components are extracted at the detection optical systems installed at different positions, so that it is possible to highly accurately determine defects.

Next, a method will be described in which a beam is applied to almost the same region on the surface of a sample at multiple times to inspect the sample highly sensitively while suppressing damage to the sample. The stages supporting the sample translate in the radial direction (the R-direction) while rotating at almost a constant speed. A feed pitch refers to a distance that translates in the radial direction at nearly one turn. The stages rotate and translate in the radial direction to spirally scan the entire surface of the sample. This embodiment is characterized in that the lighting optical system 401 linearly illuminates the sample to increase the illumination field length more than the feed pitch length, whereby applying light to almost the same region on the sample at plural times. In the following, this inspection method will be described in detail.

Figure 16:
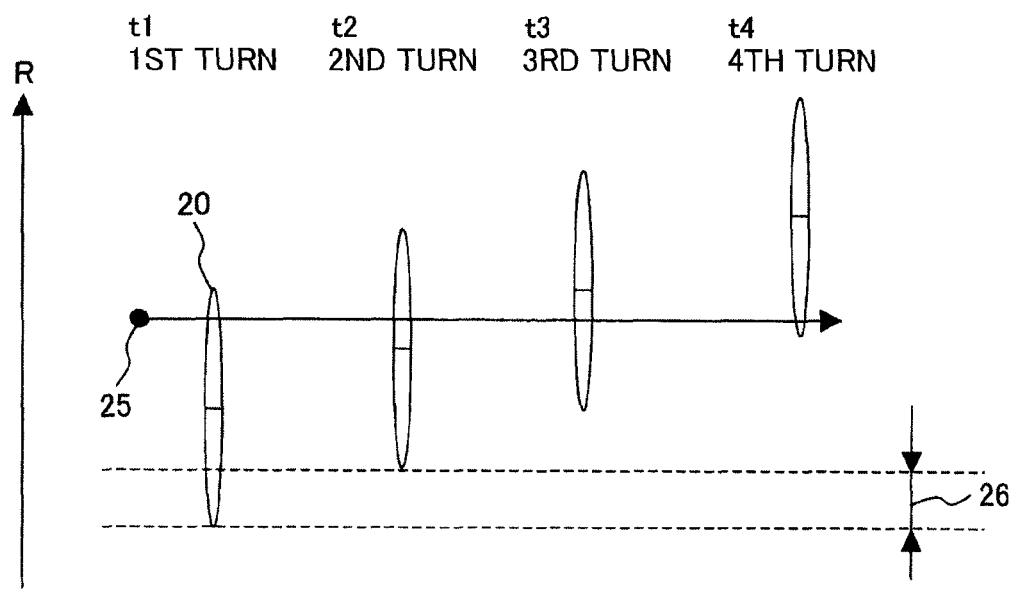
FIG. 16 is a plan view illustrating a wafer, showing the positional relationship between lighting positions and a defect from the first to fourth turn of the wafer according to the sixth embodiment.

First, a method of illuminating almost the same region on the sample at plural times will be described with reference to FIG. 16. FIG. 16 is an illustration in the case where the length of an illumination field 20 is more than four times and less than five times of a feed pitch 26 and a defect 25 passes through the illuminated region four times. When the defect 25 passes through the illuminated region in the first time at time t1, a wafer makes nearly one turn at time t2. The illuminated region goes in the radial direction almost at a distance of the feed pitch 26, and the defect 25 passes through the illuminated region again. After that, the wafer makes nearly one turn at time t3 and time t4, and the defect 25 passes through the illuminated region. In other words, in the case of FIG. 16, the defect 25 passes through the illuminated region four times, and light detected every time is added at the analog circuit or the signal processing unit. In these operations, illuminated light has different polarization conditions in the longitudinal direction of the illuminated region as shown in the light field 320 in FIG. 15A, so that detected signals are obtained from illuminated light under different polarization conditions between two turns in the first half and two turns in the second half. As described above, almost the same region on the sample is illuminated at multiple times to obtain signals detected under the different polarization conditions. Thus, it is possible to apply a beam at relatively low power density than the case of single beam application, and it is possible to highly sensitively detect micro defects on the sample surface with no damage to the sample caused by a temperature rise in the portion applied with the beam. The number of times of passing through the illuminated region is not necessarily four times, which may be any number of times if more than two.

Figure 17:
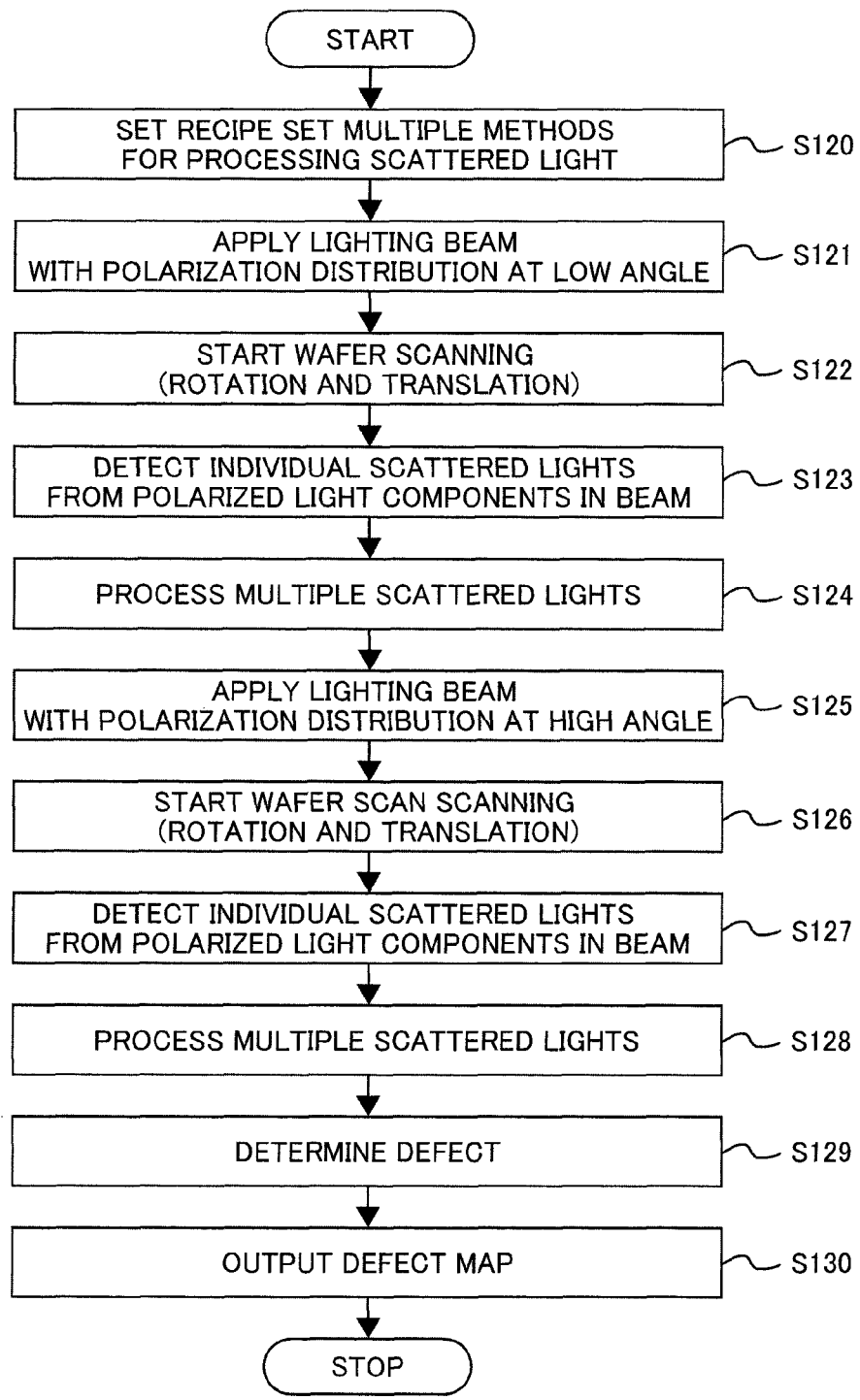
FIG. 17 is a flowchart illustrating detection process steps according to the sixth embodiment.

Next, a method of detecting defects on the sample surface using the aforementioned defect inspection apparatus will be described with reference to a defect detecting process flow shown in FIG. 17. First, a recipe is set to establish detection conditions such as a illumination direction and sensor sensitivity on a GUI (Graphic User Interface) screen, not shown, (Step S120). The settings also include the length and feed pitch of the illumination field and a processing method for a detected scattered light. A lighting beam including plural polarization components in the cross section of the beam is applied to the wafer for illumination using the low angle lighting system (Step S121). After that, wafer scanning (rotation and translation) is started (Step S122). Scattered light from polarization components in the lighting beam is detected individually and separately at the high angle detection system 403 and the low angle detection system 402 (Step S123). Plural signals of scattered light output from the sensor unit 313 and the photodiode allay 309 are processed at the signal processing unit 411 under the conditions set for the detected scattered light in recipe setting (Step S124). Subsequently, a lighting beam including plural polarization components in the cross section of the beam is applied to the wafer using the high angle lighting system (Step S125). After that, the wafer scanning (rotation and translation) is started (Step S126). Scattered light from polarization components in the lighting beam is detected individually and separately at the high angle detection system 403 and the low angle detection system 402 (Step S127). Plural signals of scattered light output from the sensor unit 313 and the photodiode allay 309 are processed at the signal processing unit 411 under the conditions set for the detected scattered light in recipe setting (Step S128). Subsequently, defects are determined based on the signals detected and processed by the low angle illumination and the high angle illumination (Step S129), and a defect map is outputted (Step S130).

With the scheme described above, the scattered lights when applying the light beam in different states of polarization are simultaneously and individually detected, so that it is possible to improve defect detection performance and to efficiently sort and size defects as similar to the first embodiment.

It is noted that in the defect detecting process flow described above, an example is shown that light is applied at a low angle and then light is applied at a high angle. However, the order may be reversed. It is also possible that defects are detected using only the detected result in applying light at a low angle, omitting the steps in applying light at a high angle (S125 to S128).

The optical dark field inspection apparatus described in FIG. 14A, as to proper use of the oblique lighting optical system and the vertical (high angle) lighting optical system, detection sensitivity can be improved using the oblique lighting optical system, whereas defect sorting performance can be improved using the vertical lighting optical system. Thus, the oblique lighting optical system and the vertical lighting optical system may be appropriately used according to applications. It is possible to improve defect sorting accuracy using the combination of the lighting optical system and the detection optical system. For convex defects, for example, it is possible to detect a large scattered light at the low angle detection optical system in oblique lighting, whereas for concave defects, it is possible to detect a large scattered light at the high angle detection optical system in applying light in the vertical direction.

Figure 18A:
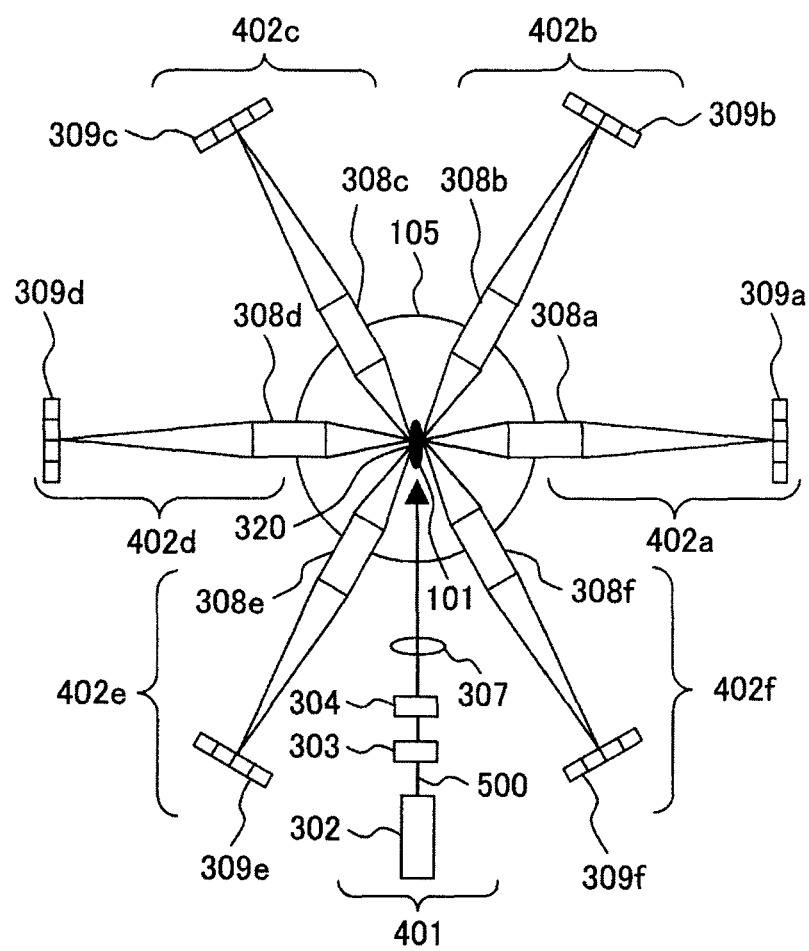
FIG. 18A is a plan view illustrating the layout of the low angle detection optical system according to the sixth embodiment.
Figure 18B:
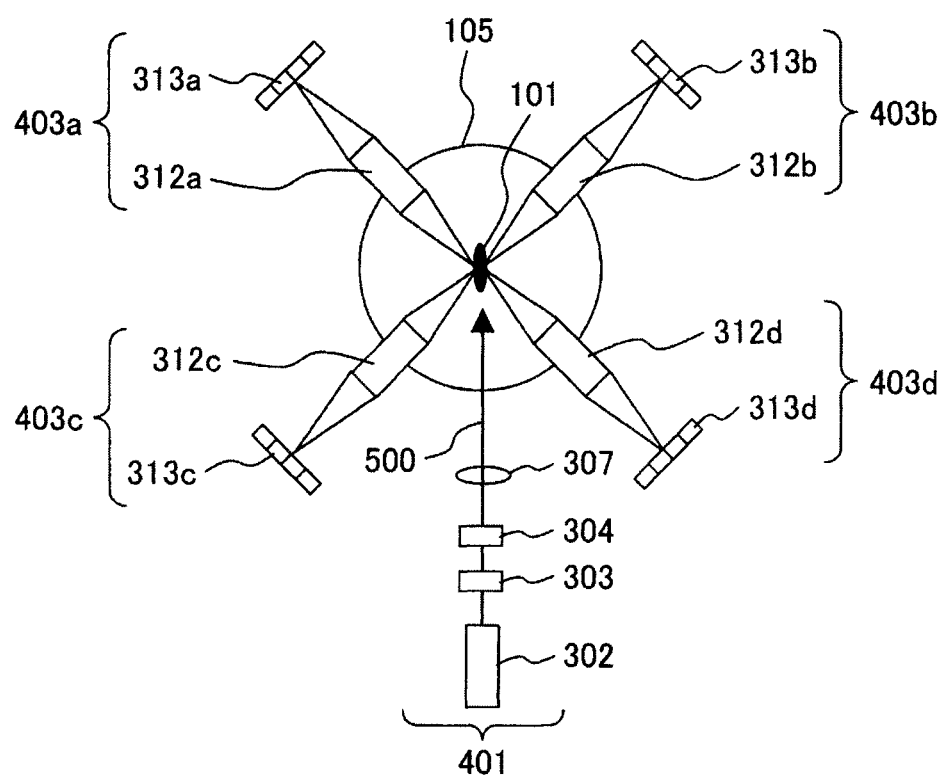
FIG. 18B is a plan view illustrating the layout of the high angle detection optical system according to the sixth embodiment.

Plural detection optical systems may be provided in different azimuth angle directions as shown in FIGS. 18A and 18B. Namely, FIG. 18A is a plan view illustrating a state in which plural low angle detection systems 402 are arranged around the application region of low angle and high angle illumination with light in the defect inspection apparatus shown in FIG. 14A, showing a wafer 105, a lighting optical system 401, and detection optical systems 402a to 402f. The detection optical systems 402a to 402f include image forming systems 308a to 308f and photodiode allays 309a to 309f. Detected signals are subjected to amplification, noise processing, and analog-to-digital conversion in an analog circuit as necessary using a configuration similar to the configuration of the signal processing and control system 420 explained in FIG. 14A. Plural optical signals scattered from almost the same region are added, defects are determined at a signal processing unit, and a defect map is displayed (not shown) at a map output unit through a CPU. Here, for the configuration of the low angle detection optical system, the image forming systems 308a to 308f are each configured by including a condenser lens, an image intensifier, an image forming lens, and a photodiode allay (not shown) as similar to the configuration explained in FIG. 15A.

FIG. 18B is a plan view illustrating a state in which plural high angle detection systems 403 are arranged around an illumination region 101 on the wafer 105 in the defect inspection apparatus shown in FIG. 14A, showing the wafer 105, the lighting optical system 401, and detection optical systems 403a to 403d. The detection optical systems 403a to 403d include condensing optical systems 312a to 312d and photodiode allays 313a to 313d. Detected signals are subjected to amplification, noise processing, and analog-to-digital conversion in the analog circuit as necessary using the configuration similar to the configuration of the signal processing and control system 420 explained in FIG. 14A. Plural optical signals scattered from almost the same region are added, defects are determined at the signal processing unit, and a defect map is displayed (not shown) at the map output unit through the CPU. Here, for the configuration of the low angle detection optical system, the detection optical systems 403a to 403d are each configured of a condenser lens, a polarizing beam splitter, a P-polarized light detecting photomultiplier tube, and an S-polarized light detecting photomultiplier tube (not shown) as similar to the configuration explained in FIG. 15B.

As described above, the detection optical systems at plural azimuth angles are used to allow inspection by selecting a detection optical system with small noise to detect many scattered lights from defects in the case where the angle characteristics of scattered light to be produced are varied depending on the size and shape of a defect, film types of a sample, and surface roughness of the sample. Thus, it is possible to improve detection sensitivity. An example is taken for the layout of the detection optical system in which six detection optical systems are provided in the different azimuth angle directions in the low angle detection optical system and four detection optical systems are provided in the high angle detection optical system in FIGS. 18A and 18B. However, the number of the detection optical systems is not limited to six and four, and the azimuth angle direction to provide the systems is not limited as well. Plural detection optical systems are not necessarily provided at almost the same angle of elevation. The systems may be provided at different angles of elevation. The detector is not necessarily provided at almost the same azimuth angle. In FIG. 17, a laser beam is applied in the direction in parallel with the longitudinal direction of the illuminated region on the wafer. However, the longitudinal direction of the illuminated region on the wafer and the direction of applying the laser beam are not necessarily almost the same, and a beam may be applied in a different direction. A beam is applied in a different direction, so that it is possible to change the distribution of scattered lights emanated from defects such as COP (crystal defect) and micro scratches (micro starches on the wafer surface), and it is possible to improve sorting performance by the combinations of detected signals from detectors at plural azimuth angles.

As described above, the invention made by the present inventors is described specifically based on the embodiments. However, the present invention is not limited to the foregoing embodiments, and it is without saying that the present invention can be variously changed and altered without deviating from the teachings of present invention.

With the downscaling of semiconductor devices such as an LSI and a liquid crystal substrate, the size of defects or foreign substances on a fine pattern that is an inspection object is a few nanometers or less. Since the size of defects or foreign substances that are objects for detection becomes thus smaller, reflected, diffracted, and scattered light from these defects and foreign substances are really weak, and it is difficult to optically detect them. However, the present invention can be for use in a method of inspecting foreign substances or defects produced in fabricating these semiconductor devices and an apparatus therefor.

The invention may be embodied in other specific forms without departing from the spirit or essential characteristics thereof. The present embodiment is therefore to be considered in all resects as illustrative and not restrictive, the scope of the invention being indicated by the appended claims, rather than by the foregoing description, and all changes which come within the meaning and range of equivalency of the claims are therefore intended to be embraced therein.

REFERENCE SINGS LIST

20 . . . illumination field
25 . . . defect
26 . . . feed pitch
100, 105 . . . semiconductor wafer
110 . . . lighting optical system
111 . . . light source
112, 112a, 112b . . . beam shaper
113, 113a, 113b . . . polarization control device
114a, 114b, 114c, 114e, 114x, 114y . . . polarization control device elements array
114i, 114j, 114k, 114l, 114m, 114n . . . pixel of polarization control device elements array
115a, 115b . . . lens
120 . . . objective lens
121a, 121b . . . luminous light beam
130 . . . spatial filter
140 . . . image forming lens
150, 150x, 150y . . . line sensor
151a, 15 155a, 155b, 155c, 155d . . . polarizer of sensor pixel
156a, 156b, 156c, 156d . . . pixels of sensor
160 . . . auto-focusing unit
170 . . . stage unit
200 . . . image processor
220 . . . manipulating unit
230 . . . controller
302 . . . laser light source
303 . . . beam expander
304 . . . homogenizer
305, 306 . . . mirror
307 . . . condenser lens 308, 308a-308f . . . image forming system
309, 309a-309f . . . photodiode allay
310 . . . stage
312 . . . condensing optical system
313 . . . CCD camera
320 . . . light field
321 . . . condenser lens
322 . . . image intensifier
323 . . . image forming lens
324 . . . analyzer
401 . . . lighting optical system
402, 402a-402f . . . detection optical system
403 . . . detection optical system
410 . . . circuit
411 . . . signal processing unit
412 . . . CPU
413 . . . map output unit
414 . . . stage controller

The invention claimed is:

1. An inspection method comprising:
illuminating a sample to be inspected with light emitted from a lighting unit;
detecting light scattered from a portion illuminated by the light with an imager having a plurality of detection pixels; and
processing a signal output from the imager by the detection of the scattered light with a signal processor to detect a defect on the sample,
wherein in the step of illuminating, the light illuminates a plurality of small regions on the sample to which the light illuminates under different polarization conditions by the small regions;
wherein in the step of detecting, the imager detects light scattered from each of the small regions, which are illuminated under the different polarization conditions by the step of illuminating, with different pixels; and
wherein in the step of processing, the signal processor processes a detected signal in each of the small regions under the different polarization conditions detected at the different pixels in the step of detecting and detects a defect on the sample.

2. The inspection method according to claim 1, wherein: in the step of detecting, the imager detects each of the small regions under the different polarization conditions at a plurality of different pixels, and the plurality of pixels have different polarization conditions for the detection.

3. The inspection method according to claim 1, wherein in the step of processing, the detected signal output from the imager corresponding to each of the small regions under the different polarization conditions is compared with a reference signal to extract a differential image, and a defect on the sample is detected from the extracted differential image.

4. The inspection method according to claim 1, wherein in the step of illuminating, the lighting unit illuminates a same place on the sample at multiple times as polarization conditions are changed and wherein in the step of detecting, the imager detects the same place on the sample at different pixels under each of the different polarization conditions.

5. An inspection apparatus comprising:
a lighting unit configured to illuminate a sample with light;
an imager having a plurality of detection pixels and configured to detect scattered light emanated from a portion on the sample illuminate with the lighting unit; and
a signal processor configured to process a signal output from the imager by the detection of the scattered light,
wherein the lighting unit includes a polarization condition setting unit configured to illuminate a plurality of small regions on the sample under different polarization conditions;
wherein the imager individually detects each of the small regions under the different polarization conditions at different pixels; and
wherein the signal processor processes a detected signal in each of the small regions under the different polarization conditions detected at the different pixels and detects a defect on the sample.

6. The inspection apparatus according to claim 5, wherein the imager detects each of the small regions under the different polarization conditions at a plurality of different pixels through filters with different polarization conditions.

7. The inspection apparatus according to claim 5, wherein the signal processor includes:
a differential image calculating unit configured to compare the detected signal in each of the small regions under the different polarization conditions detected at the different pixels of the imager with a reference signal and extract a differential image; and
a defect detecting unit configured to detect a defect on the sample from the differential image extracted at the differential image calculating unit.

8. The inspection apparatus according to claim 5, further comprising a table unit placing the sample thereon and capable of rotating and translating, wherein:
the table unit translates in one direction while rotates with the sample placed thereon, so that the lighting unit illuminates a same place on the sample at multiple times by changing the polarization conditions; and
the imager detects images of the same place on the sample at different pixels under each of the different polarization conditions.

9. An inspection apparatus comprising:
a low angle lighting unit configured to apply a first illumination of light to a sample from a first elevation angle direction;
a high angle lighting unit configured to apply a second illumination of light to the sample from a second elevation angle direction;
a low angle imager having a plurality of detection pixels and configured to detect light scattered in a third elevation angle direction from a portion on the sample illuminated with the light from the low angle lighting unit or the high angle lighting unit;
a high angle imager configured to detect scattered light scattered in a fourth elevation angle direction from the portion on the sample illuminated with the light from the low angle lighting unit or the high angle lighting unit; and
a signal processor configured to process signals output from the low angle imager and the high angle imager by the detection of the scattered light and detect a defect on the sample, wherein:
the low angle lighting unit and the high angle lighting unit include a polarization condition setting unit configured to illuminate a plurality of small regions in a region on the sample to which the lights emitted from the low angle lighting unit and the high angle lighting unit are illuminated under different polarization conditions;
the low angle imager individually detects each of the small regions under the different polarization conditions at different pixels; and
the signal processor processes the detected signal in each of the small regions under the different polarization conditions detected at the different pixels of the low angle imager and signals detected using the high angle imager and detects a defect on the sample.

10. The inspection apparatus according to claim 9, further comprising a table unit placing the sample thereon and capable of rotating and translating, wherein:
the table unit translates in one direction while rotates with the sample placed thereon, so that the low angle lighting unit and the high angle lighting unit illuminate a same place on the sample at multiple times by changing the polarization conditions; and
the low angle imager detects images of the same place on the sample at different pixels under different polarization conditions.

* * * * *